United States Patent
Suga et al.

(10) Patent No.: US 9,701,993 B2
(45) Date of Patent: Jul. 11, 2017

(54) ARTIFICIAL TRANSLATION/SYNTHESIS SYSTEM

(75) Inventors: Hiroaki Suga, Tokyo (JP); Hiroshi Murakami, Tokyo (JP); Yuki Goto, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 808 days.

(21) Appl. No.: 13/816,911

(22) PCT Filed: Aug. 26, 2011

(86) PCT No.: PCT/JP2011/069251
§ 371 (c)(1),
(2), (4) Date: Feb. 13, 2013

(87) PCT Pub. No.: WO2012/026566
PCT Pub. Date: Mar. 1, 2012

(65) Prior Publication Data
US 2013/0217599 A1    Aug. 22, 2013

(30) Foreign Application Priority Data

Aug. 27, 2010  (JP) .................................. 2010-190315

(51) Int. Cl.
*C12P 21/00* (2006.01)
*C12N 15/67* (2006.01)
*C12P 21/02* (2006.01)

(52) U.S. Cl.
CPC .............. *C12P 21/00* (2013.01); *C12N 15/67* (2013.01); *C12P 21/02* (2013.01)

(58) Field of Classification Search
None
See application file for complete search history.

(56) References Cited

U.S. PATENT DOCUMENTS

2010/0168380 A1   7/2010  Suga et al.

FOREIGN PATENT DOCUMENTS

EP       2 141 175 A1   1/2010
WO    2008/117833 A1   10/2008

OTHER PUBLICATIONS

Forster et al., "Programming peptidomimetic syntheses by translating genetic codes designed de novo", Proceedings of the National Academy of Sciences USA, 2003, vol. 100, No. 11, pp. 6353-6357.
Goto et al., "New strategies for genetic code reprogramming; dual genetic code and artificial division of codon boxes", Peptide Science, 2010, p. 62.
Hayashi et al., "Ribosomal synthesis of nonstandard cyclic peptides and its application to drug discovery", Journal of Japanese Biochemical Society, Jun. 25, 2010, vol. 82, No. 6, pp. 505-514.
Hitomi et al., "Artificial Division of Codon Boxes for Assignments of Multiple Non-proteinogenic Amino Acids", Peptide Science, 2009, pp. 17-18.
International Search Report for PCT/JP2011/069251 mailed on Oct. 4, 2011.
Josephson et al., "Ribosomal Synthesis of Unnatural Peptides", J. Am. Chem. Soc., 2005, vol. 127, pp. 11727-11735.
Kawakami et al., "Messenger RNA-Programmed Incorporation of Multiple N-Methyl-Amino Acids into Linear and Cyclic Peptides", Chemistry & Biology, 2008, vol. 15, pp. 32-42.
Murakami et al., "A highly flexible tRNA acylation method for non-natural polypeptide synthesis", Nature Methods, vol. 3, No. 5, 2006, pp. 357-359.
Chinese Office Action issued in Chinese Patent Application No. 201180052318.9 on May 16, 2014.
Extended European Search Report, dated Sep. 20, 2016, for corresponding European Application No. 11820026.0.
Goto et al., "Flexizymes for genetic code reprogramming," Nature Protocols, vol. 6, No. 6, 2011 (published online May 12, 2011), pp. 779-790.
Goto et al., "Translation initiation with initiator tRNA charged with exotic peptides," Journal of the American Chemical Society, vol. 131, 2009, pp. 5040-5041.
Higuchi et al., "Programmed synthesis of natural product-like non-standard peptides using the translation system and its application," Journal of Synthetic Organic Chemistry, vol. 68, No. 3, Apr. 2010, pp. 217-227, with English abstract.
Kang et al., "Synthesis of the backbone cyclic peptide sunflower trypsin inhibitor-1 promoted by the induced peptidyl-tRNA drop-off," Angewandte Chemie International Edition, vol. 50, 2011 (published online Jan. 24, 2011), pp. 2159-2161.
Ohshiro et al., "Ribosomal synthesis of backbone-macrocyclic peptides containing γ-Amino acids," ChemBioChem, vol. 12, 2011 (published online on Apr. 19, 2011), pp. 1183-1187.

*Primary Examiner* — Nancy Treptow
(74) *Attorney, Agent, or Firm* — Birch, Stewart, Kolasch & Birch, LLP

(57) ABSTRACT

A new artificial translation-synthesis system of adding tRNAs binding special amino acids to the in vitro translation system and synthesizing peptides with special amino acids incorporated thereto according to a dual genetic code table and an artificial codon box division.

11 Claims, 12 Drawing Sheets

Figure 1

ARTIFICIAL TRANSLATION/SYNTHESIS SYSTEM

TECHNICAL FIELD

The present invention relates to a novel artificial translation-synthesis system using a dual genetic code table and an artificial codon box division. The present inventors named the method, the "Flexible In-vitro Translation (FIT) system".

BACKGROUND ART

1. Merits of Translation-Synthesis System and Technical Limitations of the Same

Translation is a protein synthesis carried on universally in the living body through which a precise synthesis of protein is achieved by the ribosome sequentially connecting 20 types of proteinogenic amino acids using mRNA, which encodes genetic information, as the blueprint. Considering that no other system can polymerize such variety of building blocks with precise sequence control, translation is the greatest available precision synthesis system for synthesizing compounds. Translation-synthesis holds many advantages over conventional chemical synthesis methods, especially when it is used for constructing a peptide library and isolating functional peptides therefrom.

The translation reaction is a type of template synthesis that depends on the mRNA sequence. So, a reaction based on mRNAs (or corresponding DNAs) of random sequences enables a random peptide library to be built in one effort. In addition, such translation reaction can easily re-synthesize and induce deconvultion (which means, in the present technology, dividing a condensed active peptide group from the random peptide library and determining their sequences) of library compounds, since mRNA can be amplified and its sequence can be read by molecular biological means. Further, the reaction combined with an in vitro display technology, represented by the mRNA display method, allows each peptide produced from the translation to be directly tagged by its template mRNA. In other words, a tag that can be amplified and read will be attached to each peptide molecule in the library. Selection and isolation of active peptides based on molecular evolution engineering, which are impossible from a conventional chemical synthesis library, are possible by selecting from the above library only an active species that binds the target protein, and then repeating the process using RT-PCR to amplify and translate again the corresponding mRNA.

In summary, the merits of constructing a peptide library in the translation system include the following: 1) a high diversity can be easily obtained (to $10^{13}$ or higher); 2) deconvolution can be easily performed; 3) the library can be amplified; 4) selection can be performed using the in vitro display technology.

The ribosomal translation apparatus enables a highly functional peptide library to be efficiently constructed as described above, but the fact that it specializes in creating natural proteins and peptides restricts the system to synthesize only polypeptides from the 20 types of proteinogenic amino acids, which is a fatal defect. That is, peptides comprising "special (non-standard) amino acids" which are more diverse in structure and functional groups basically cannot result from translation-synthesis. "Special amino acids" of the present specification generally refer to amino acids with structures differing from proteinogenic amino acid witnessed in protein. That is, non-proteinogenic amino acid or artificial amino acid, created by chemically changing or modifying part of the side chain structure of proteinogenic amino acid, D-amino acid, N-methyl amino acid, N-acylamino acid, and β-amino acid are all included in "special amino acids".

2. Currently-Reported Methods for Altering Genetic Codes

Several methods for altering genetic codes to mitigate the fatal defect of the ribosomal translation apparatus, namely, that it can synthesize only peptides from the 20 types of proteinogenic amino acids, have been reported to date. The codon-amino acid mapping in translation is known as a genetic code, and 20 types of amino acids are strictly defined for use. The concept is to enable the use of amino acids other than the 20 types by artificially altering the mapping.

A means referred to as the expansion of genetic codes utilizes the termination codon or 4 artificial base condons, which are not used for specifying amino acids in the naturally occurring translation, by assigning a "$21^{st}$ amino acid" which is not a proteinogenic amino acid to such codons, thereby enabling synthesis of proteins and peptides that contain amino acids other than the proteinogenic amino acid. However, the limit in the number of the termination codon and the 4 available base codons placed an upper limit on the types of non-proteinogenic amino acids that can be used simultaneously (a maximum of 3 types and a standard of 2 or 1 type are reported to date). Meanwhile, a genetic code reprogramming method (rewriting by initialization), which assigns non-proteinogenic amino acids to vacant codons prepared by removing proteinogenic amino acids from the system, was developed in the 2000s and at least 4 types of non-proteinogenic amino acids were made available (Non-patent Documents 1 to 3). However, the genetic code reprogramming method is also defective in that it cannot use all 20 proteinogenic amino acids due to its requirement to remove a few proteinogenic amino acids, which limits the number of proteinogenic amino acids available for use. In other words, the conventional genetic-code alteration methods were limited in the number of usable non-proteinogenic amino acids or proteinogenic amino acids, and they did not allow a flexible use of desired amino acids.

Further, special amino acids (e.g. D-amino acid and N-methyl amino acid), whose structure differ greatly from natural L-α-amino acids, were generally rejected as substrates by the translation system and were not taken into peptide synthesis even if they were assigned to vacant codons by the above method. That is, special amino acids were amino acids that were not easily taken in or not taken in at all by peptide chains in the normal translation system or the conventional altered translation system.

CITATION LIST

Non-Patent Documents

Non-Patent Document 1: Forester, A. C. et al.: Proc. Natl. Acad. Sci. USA, Vol. 100, p. 6353-6357 (2003)

Non-Patent Document 2: Josephson, K., Hartman, M. C., Szostak, J. W.: J. Am. Chem. Soc., Vol. 127, p. 11727-11735 (2005)

Non-Patent Document 3: Murakami, H. et al.: Nat. Mathods, Vol. 3, p. 357-359 (2006)

SUMMARY OF INVENTION

Technical Problem

In conventional reprogramming of genetic codes, the vacant codons to which special (non-standard) amino acids were assigned were prepared by removing some proteinogenic amino acids; hence, the removed proteinogenic amino acids were no longer available for use.

The object of the present invention is to provide a translation-synthesis system that allows the simultaneous use of many special amino acids as well as all proteinogenic amino acids.

Solution to Problem

The present inventors completed a novel artificial translation-synthesis system (FIT system) that allows, by principle, the simultaneous use of 40 or more types of amino acids by proposing and establishing two new concepts concerning the alteration of genetic codes. The concepts are described below in the order of (1) dual genetic codes, and (2) an artificial division of the codon box.

1. Dual Genetic Codes

In a natural universal genetic code table, a codon defines only a single amino acid. However, in exceptional cases of translation in prokaryotes, the AUG codon specifies fMet (formylmethionine) in the initiation reaction and Met (methionine) in the subsequent elongation reaction. Strictly speaking, the codon specifies two structurally different amino acids, fMet and Met, in initiation and elongation respectively. The present inventors considered that other codons may also be used in both initiation and elongation, and be made to correspond to different amino acids in the two stages. The idea is to prepare a new artificial codon table specifically for the initiation reaction in addition to that for the elongation reaction, and have the two tables functioning simultaneously; this is the new "dual genetic code" concept.

In comparison to the natural translation apparatus, where only AUG functions as the initiation codon, the initiation reaction of dual genetic codes has multiple codons other than AUG participating in it. Further, these artificial initiation codons are each a codon that specifies two different amino acids in the initiation reaction and the elongation reaction, or a "dual sense codon". Since multiple artificial initiation residues function simultaneously in a translation system using dual genetic codes, a peptide library holding various N-terminal structures may be synthesized with one effort. This is a large merit compared to conventional translation systems in which the number of initiation residues functioning in one translation system is limited to only one.

2. Artificial Division of the Codon Box

Although dual genetic codes provide a much more diverse variety of initiation residues, the use of several proteinogenic amino acids still needs to be abandoned when special amino acids are used in an elongation reaction. A reprogramming of genetic codes that artificially divides codon boxes solves such problem.

In a universal genetic code table, multiple codons may define the same amino acid. For example, the codon box of GUN is occupied completely by Val. According to the concept of the artificial division of a codon box, such codon box is divided in two with one section specifying the original proteinogenic amino acid and the other section defining a separate special amino acid [Genetic codes for elongation only on the right side of FIG. 1; Val is assigned to GU(A/G) and the desired special amino acid (Xa3) is assigned to GU(U/C) in the GUN box.] In principal, 11 types of special amino acids in addition to 20 natural amino acids can be used simultaneously in the elongation reaction of such translation system.

3. A New Artificial Translation-Synthesis System Combining the Dual Genetic Code Table and the Artificial Codon-Box Division Combining the dual genetic code table and the artificial codon-box division enables the creation of a translation system containing a largely increased number of amino acids that can be simultaneously used. That is, multiple dual sense codons used in the dual genetic code table are placed in artificially-divided codon boxes. In other words, 4 different amino acid residues are assigned within a single codon box. Further, a special amino acid can be assigned to a termination codon. This enables the simultaneous use of all 20 types of proteinogenic amino acids+ at least 11 types of artificial initiation residues+a maximum of 12 types of special amino acids in a translation system. Dual sense codons can further be placed in sections other than the artificially divided codon boxes; all together, the number of types of amino acids that can be used simultaneously in the translation system will easily be 40 or higher.

FIG. 2 compares the FIT system with a conventional synthesis of a cyclic peptide library by rewriting the initiation reaction (Goto et al., ACS Chem. Biol., 2008, 3, 120-129; WO 2008/117833 "A synthesis method of a cyclic peptide compound"). FIG. 2a shows a conventional method of rewriting the initiation reaction, and 2b shows the FIT system of the present invention. In a conventional method (FIG. 2a), the initiation residue:

☆ [Formula 1]

in a single translation system was limited to one type, and Met could not be used simultaneously. In contrast, in the FIT system, a library can be obtained which consists of peptides that are subject to cyclization of various structures and comprise multiple special amino acids.

Further, the use of proteinogenic amino acids in the elongation reaction was limited to the extent that special amino acids were used. The FIT system, however, allows multiple types of altered initiation residues to be used simultaneously in addition to fMet, and further allows multiple special amino acids and all proteinogenic amino acids to be incorporated in the elongation reaction.

The gist of the present invention is as follows.
(1) A method for synthesizing a peptide, comprising adding tRNAs charged with special amino acids to an in vitro translation system to allow synthesis of a peptide with the special amino acids incorporated therein, wherein a special amino acid is incorporated onto an N-terminal of peptide by the special amino acid functioning as an initiation amino acid in a translation initiation reaction on a ribosome, wherein the special amino acid is bound to an initiator tRNA that contains an anticodon complementary to a codon of a translation initiation site of an mRNA; and a special amino acid is incorporated onto a position specified by an anticodon of an elongator tRNA charged with the special amino acid according to an altered genetic code table that assigns special amino acids to a part of a plurality of codons that specify one type of proteinogenic amino acid in a universal genetic code table, in a peptide chain elongation reaction.
(2) The above method, wherein the tRNAs charged with special amino acids are prepared by an in vitro aminoacylation of tRNAs formed by an in vitro transcription-synthesis.
(3) The above method, wherein the altered genetic code table for elongation reaction assigns special amino acids to a part of a plurality of codons that independently specify Leu, Val, Ser, Pro, Thr, Ala, Arg, and Gly in the universal genetic code table.

(4) The method according to (3), wherein the altered genetic code table for elongation reaction maintains original proteinogenic amino acids for 2 of 4 or 6 codons that independently specify Leu, Val, Ser, Pro, Thr, Ala, Arg, Gly in the universal genetic code table and assigns arbitrary special amino acids to remaining codons.

(5) The above method, wherein the altered genetic code table for elongation reaction further assigns special amino acids to some termination codons.

(6) The above method, wherein the cellular translation system includes a set of tRNA and ARS for proteinogenic amino acids, in which the tRNA is that formed by in vitro transcription-synthesis instead of a natural tRNA and the ARS (aminoacyl tRNA synthetase) is that which can specifically bind a proteinogenic amino acid to the tRNA, but it does not include any natural tRNA.

(7) The above method, wherein the codon of the translation initiation site is an artificial initiation codon consisting of AUG or any other triplet sequence.

(8) The method according to (7), wherein the artificial initiation codon is AUG, UGG, AUC, ACC, UCG, AAC, GCC, GGC, CCG, CGG, GGG, or AUA.

(9) The above method, wherein a codon with a same sequence can be assigned to different special amino acids for the translation initiation reaction and the elongation reaction by binding different special amino acids to an initiator tRNA and an elongation tRNA, the tRNAs having anticodons of a same sequence.

(10) The method according to (8), wherein a codon of a same sequence assigned to different special amino acids in a translation initiation reaction and an elongation reaction is AUG, UGG, AUC, ACC, UCG, or AAC.

(11) The above method, wherein multiple peptides having N-terminal amino acids that differ from each other are synthesized in one translation system by using multiple mRNAs as templates, the mRNAs having artificial initiation condos that differ from each other, and
adding aminoacyl initiator tRNAs consisting of initiator tRNAs binding with different artificial initiation residues, the initiator tRNAs including anticodons that are each complementary to an artificial amino acid, to synthesize peptide.

(12) The method of (1), wherein a nucleic acid library consisting of template nucleic acids having various sequences is synthesized, by adding initiator tRNAs having various anticodon sequences binding arbitrary special amino acids, and elongator tRNAs having various anticodon sequences and binding arbitrary special amino acids to an in vitro translation system.

(13) The method of (12), wherein a nonstandard peptide is bound to a template nucleic acid that codes for the peptide when it is synthesized.

(14) A kit for translation-synthesis of a nonstandard peptide, comprising at least:
(i) an mRNA, wherein a region encoding a peptide comprises
(a) an artificial initiation codon that specifies an artificial initiation residue, and
(b) elongator codons that specify special amino acids;
(ii) an aminoacyl tRNA for an artificial initiation residue and an aminoacyl tRNA for a special amino acid, which are
(c) an initiator tRNA having an anticodon complementary to the artificial initiation codon of (a) and charged with an artificial initiation residue, and (d) an elongator tRNA having an anticodon complementary to the elongation codon of (b) and charged with a special amino acid;
(iii) a set of tRNA and ARS for proteinogenic amino acid comprising a proteinogenic amino acid, an artificial tRNA that does not comprise a modified base group, and an ARS for binding a proteinogenic amino acid to the artificial tRNA; and
(iv) an isolated ribosome.

Advantageous Effects of Invention

The present invention enables extensive enhancement of the diversity of nonstandard peptides to be synthesized by the in vitro translation system. Further, it enables peptide synthesis with a group of easily controllable factors that are smaller in number than conventionally known translation systems, and it can be easily produced.

The peptide library constructed using the translation system (FIT system) of the present invention can cover a wider sequence space than conventional libraries, and is seen to potentially provide great merits in the search for a physiologically active peptide.

BRIEF DESCRIPTION OF DRAWINGS

FIG. 1 shows examples of artificial genetic codes proposed by the present inventors. Two codon tables, one for initiation reaction only (left) and one for elongation reaction only (right), are used.

 [Formula 2]

respectively show artificial initiation residues•special amino acids•a proteinogenic amino acid.

Figure 2:
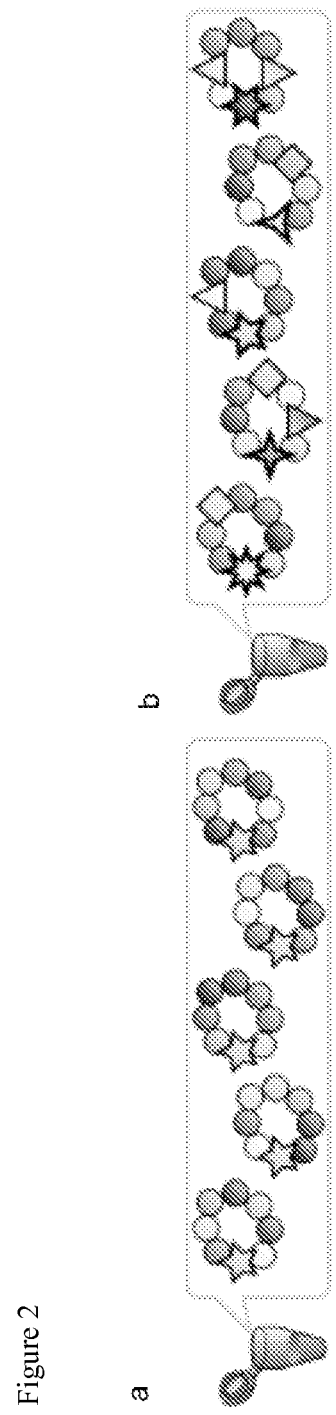
FIG. 2 is a conceptual illustration of the synthesis of a cyclic peptide library through translation-synthesis. Compared are (a) a conventional method of rewriting initiation reaction and (b) the FIT system of the present invention. The following symbols.
Figure 3:
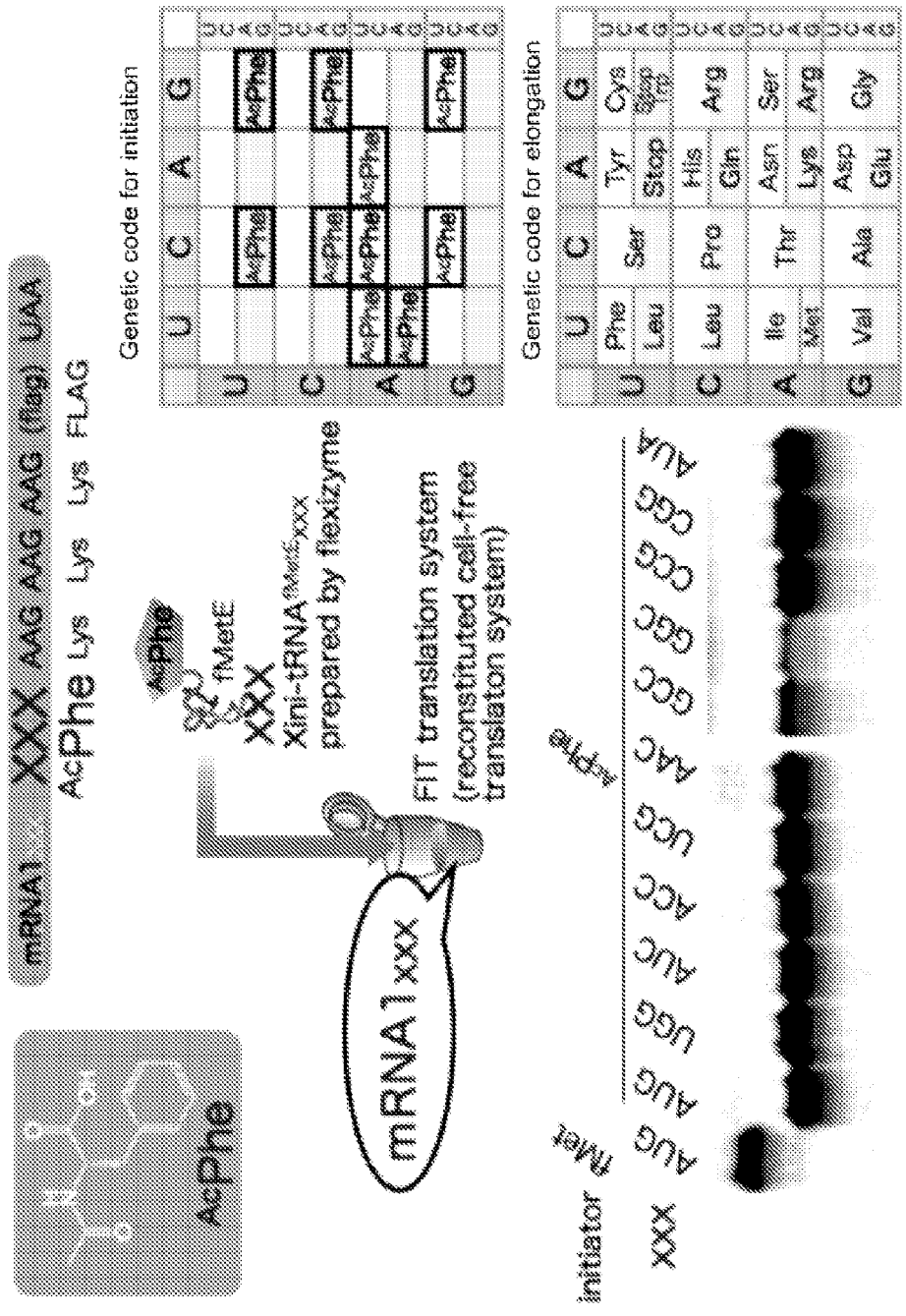

FIG. 3 shows an experiment result confirming that multiple codons other than AUG function as artificial initiation codons.

Figure 4:
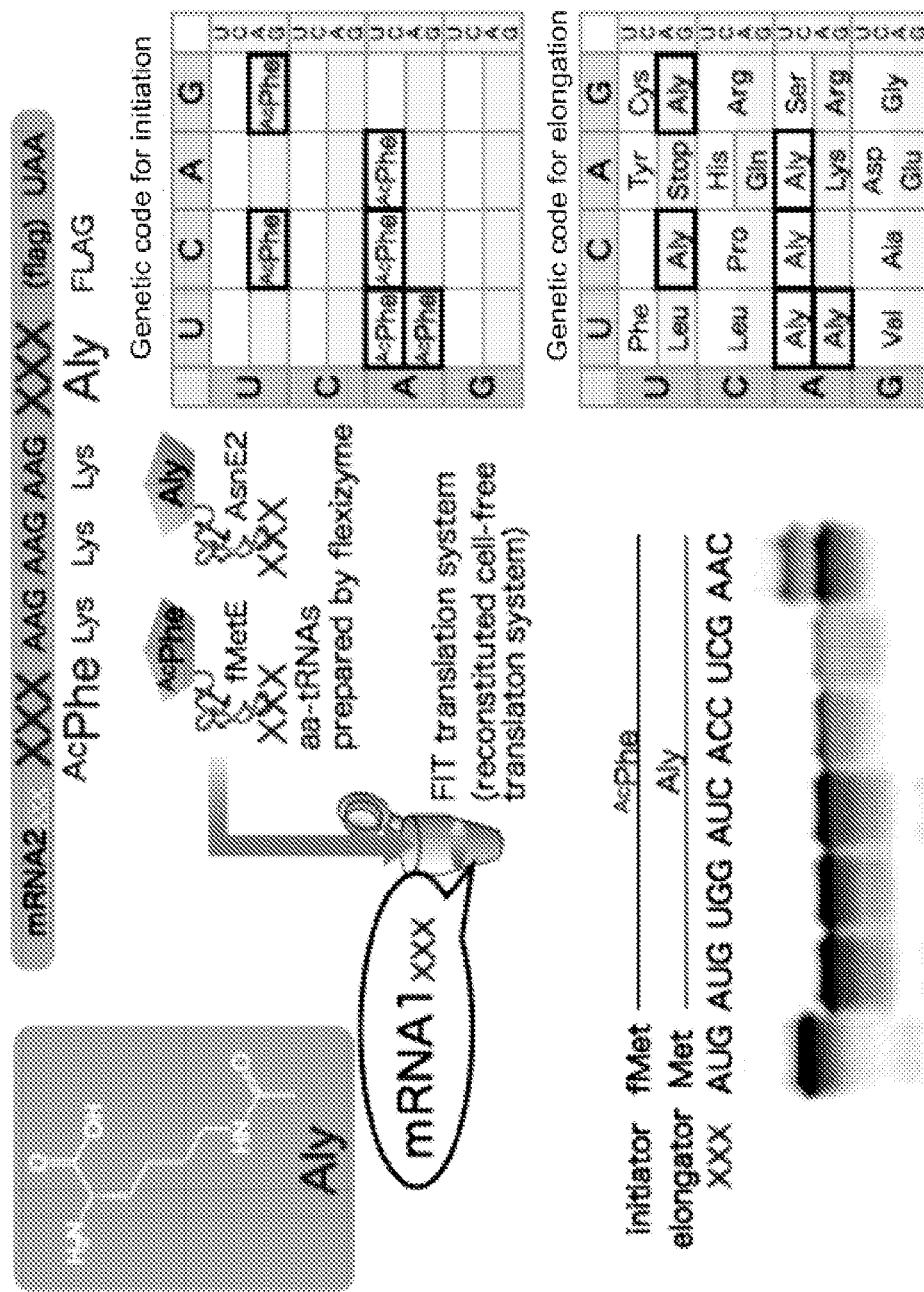

FIG. 4 shows an experiment result confirming that the same codon functions in both initiation and elongation, and codes for different amino acids.

Figure 5:
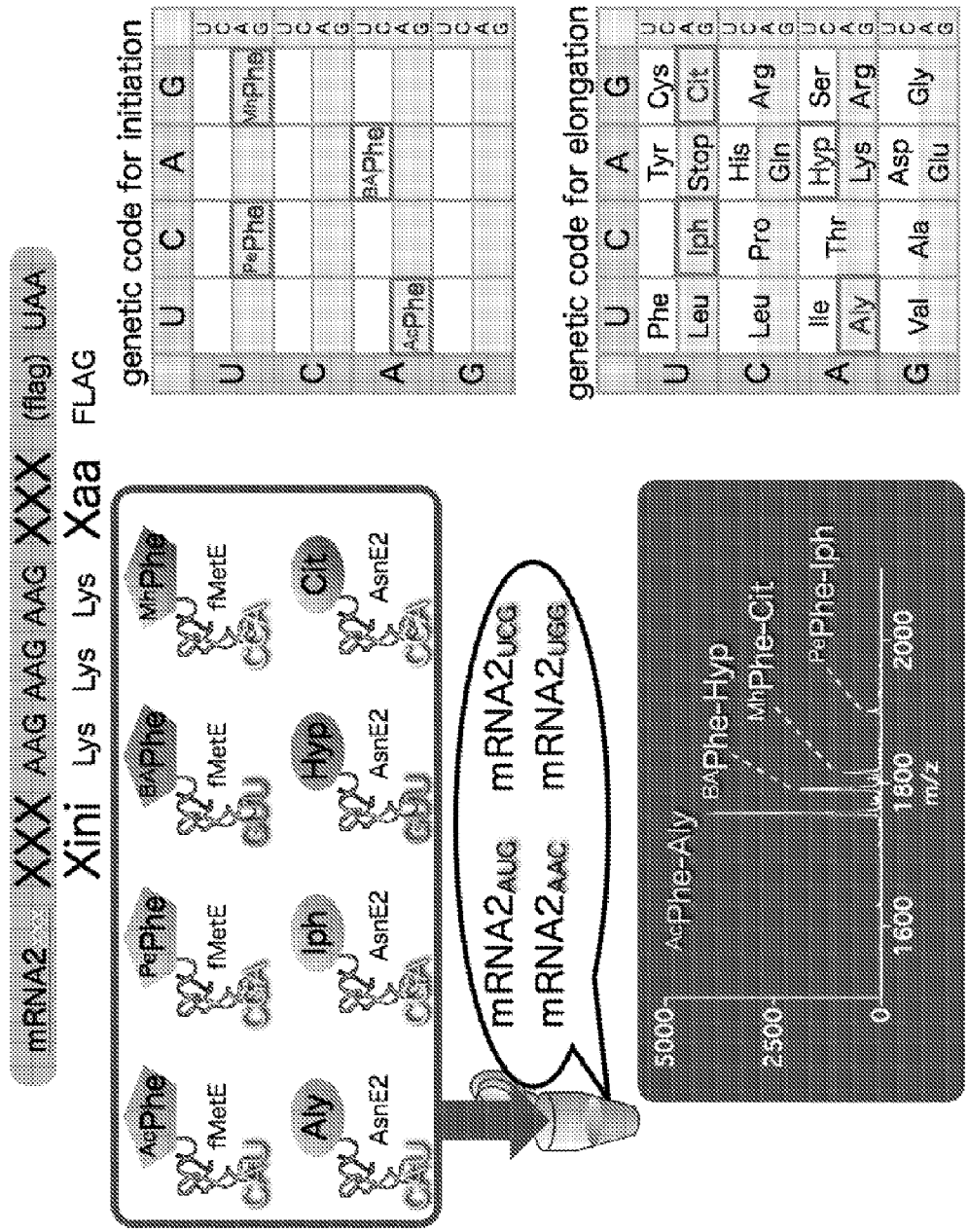

FIG. 5 shows an experiment result of using a dual genetic code to simultaneously use a total of 8 types of special amino acids and artificial initiation residues.

Figure 6:
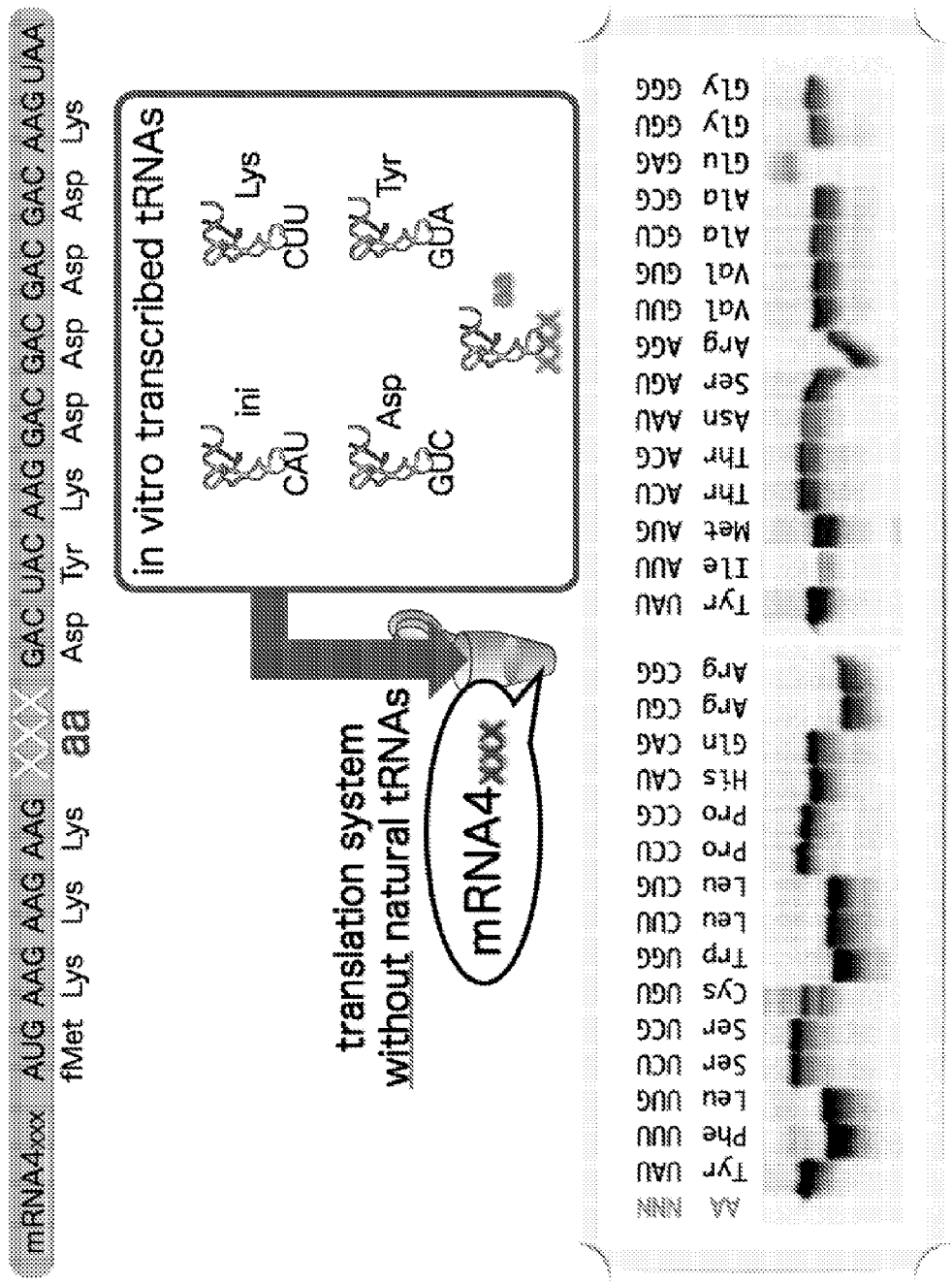

FIG. 6 shows an experiment result confirming that tRNA, resulting from in vitro transcription-synthesis using T7 RNA polymerase, functions in a translation reaction.

Figure 7:
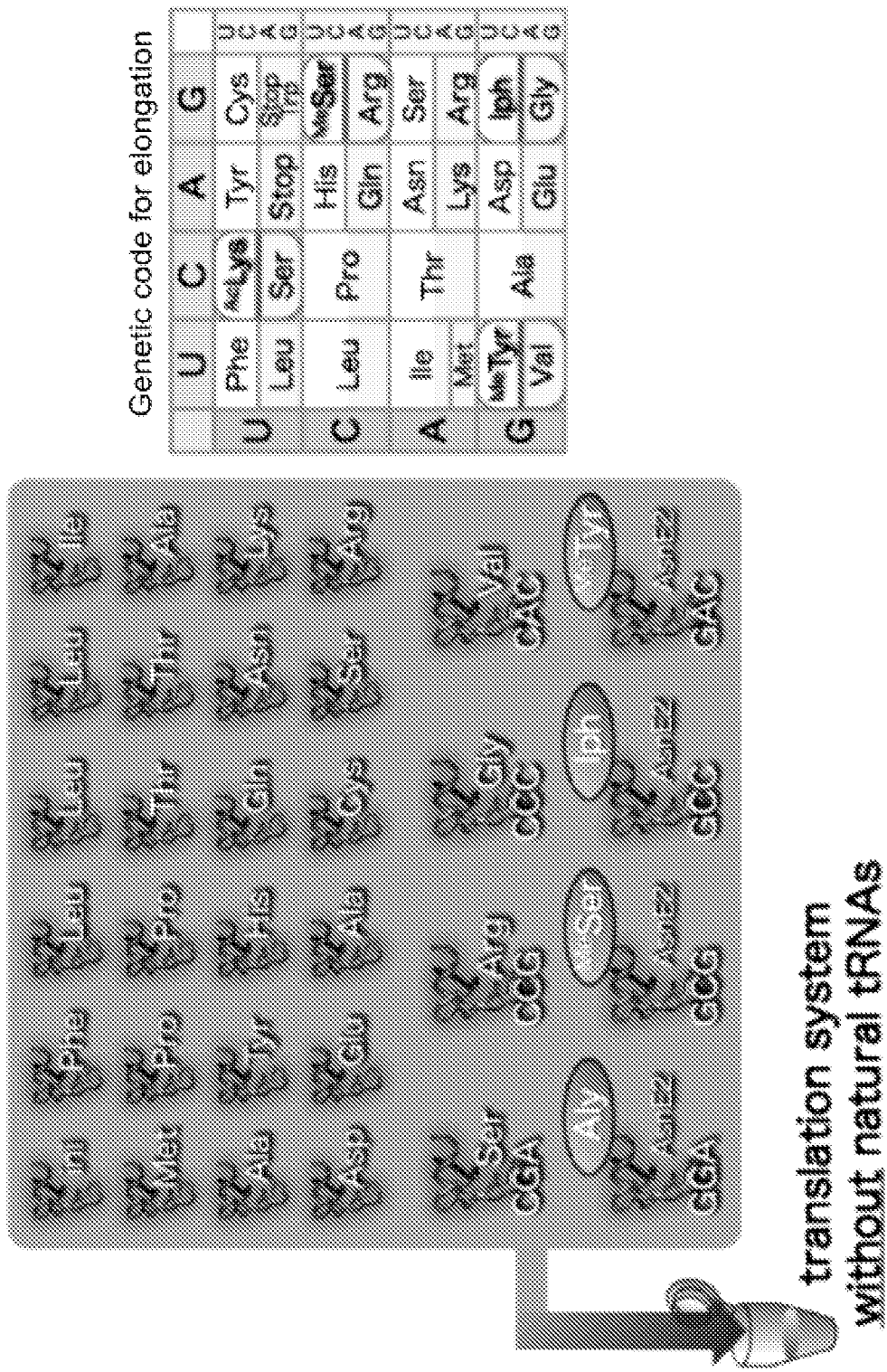

FIG. 7 is a conceptual illustration of an experiment to divide codon boxes.

Figure 8:
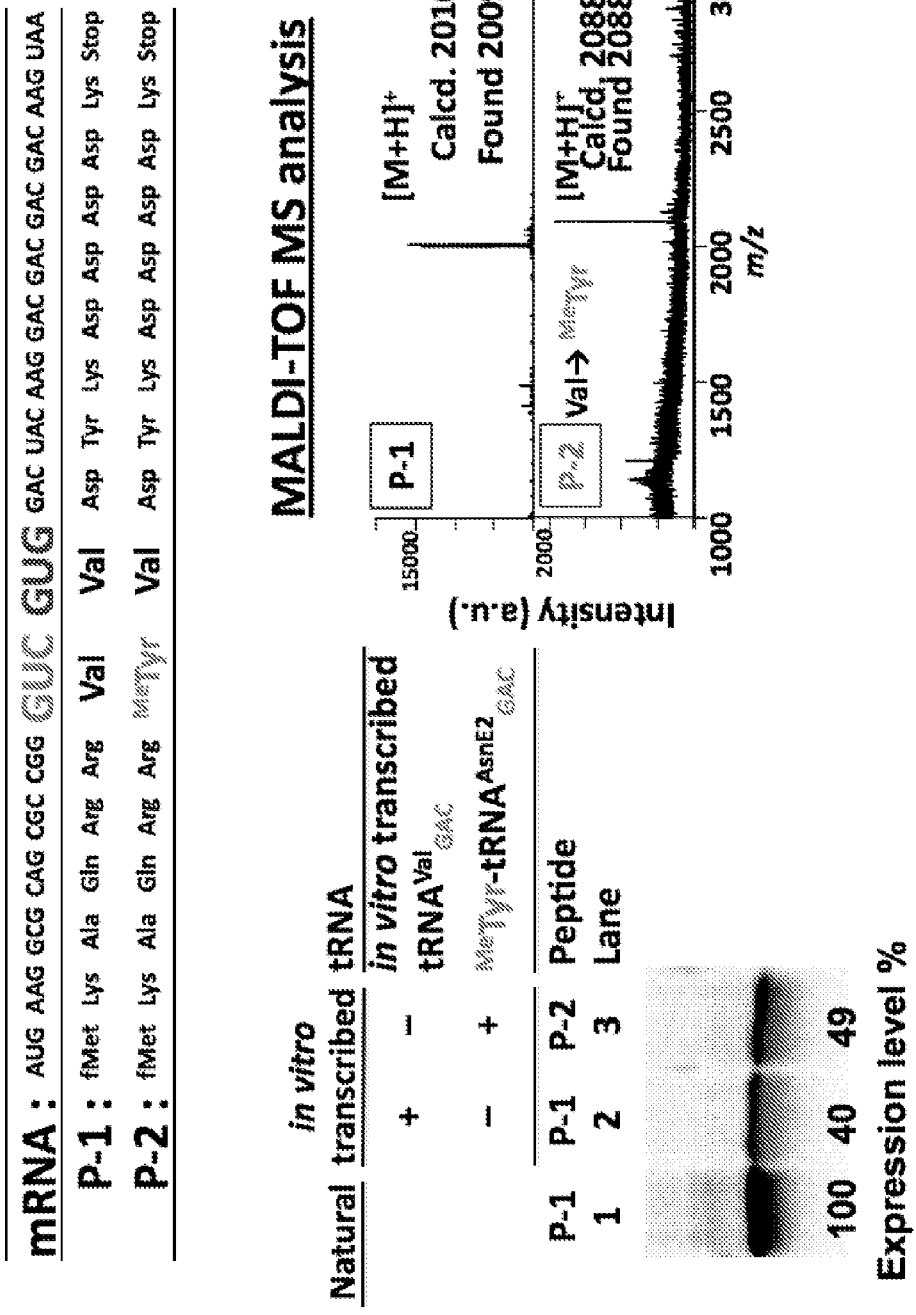

FIG. 8 shows an experiment result of artificially dividing a codon box (the Val codon box).

Figure 9:
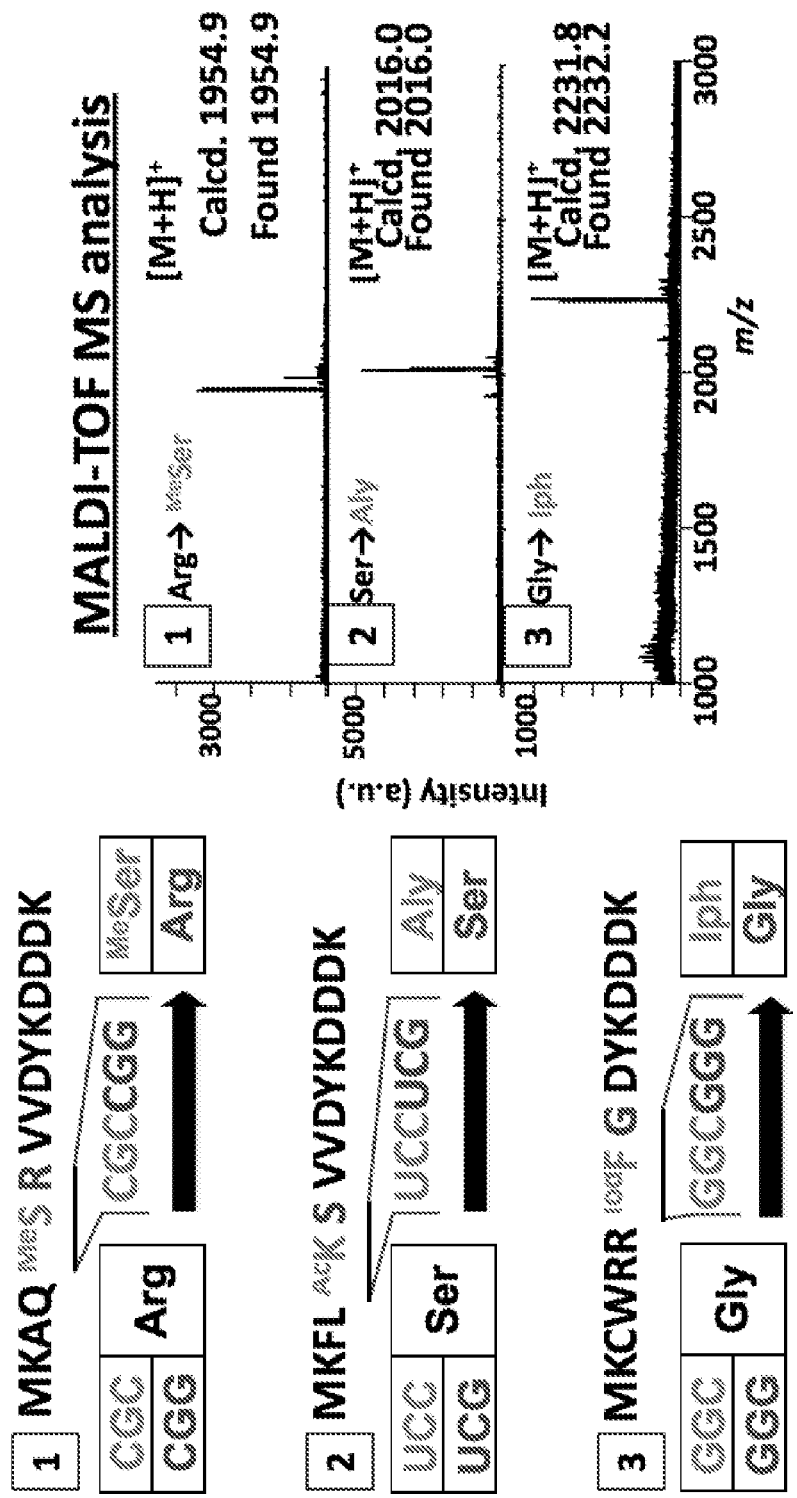

FIG. 9 shows an experiment result of artificially dividing codon boxes (codon boxes that are not Val codon box).

Figure 10:
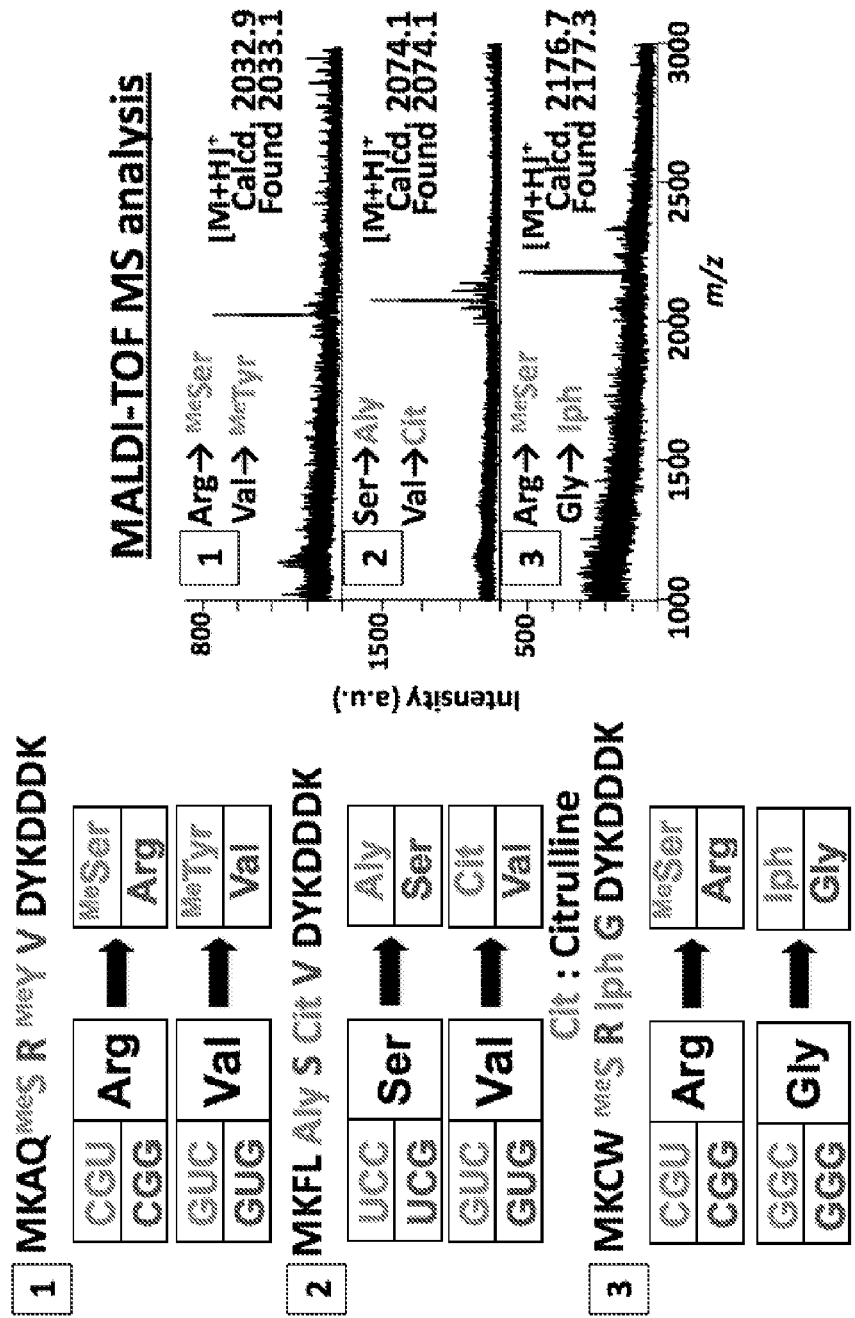

FIG. 10 shows an experiment result of artificially dividing codon boxes (in which two codon boxes are divided with one effort).

Figure 11:
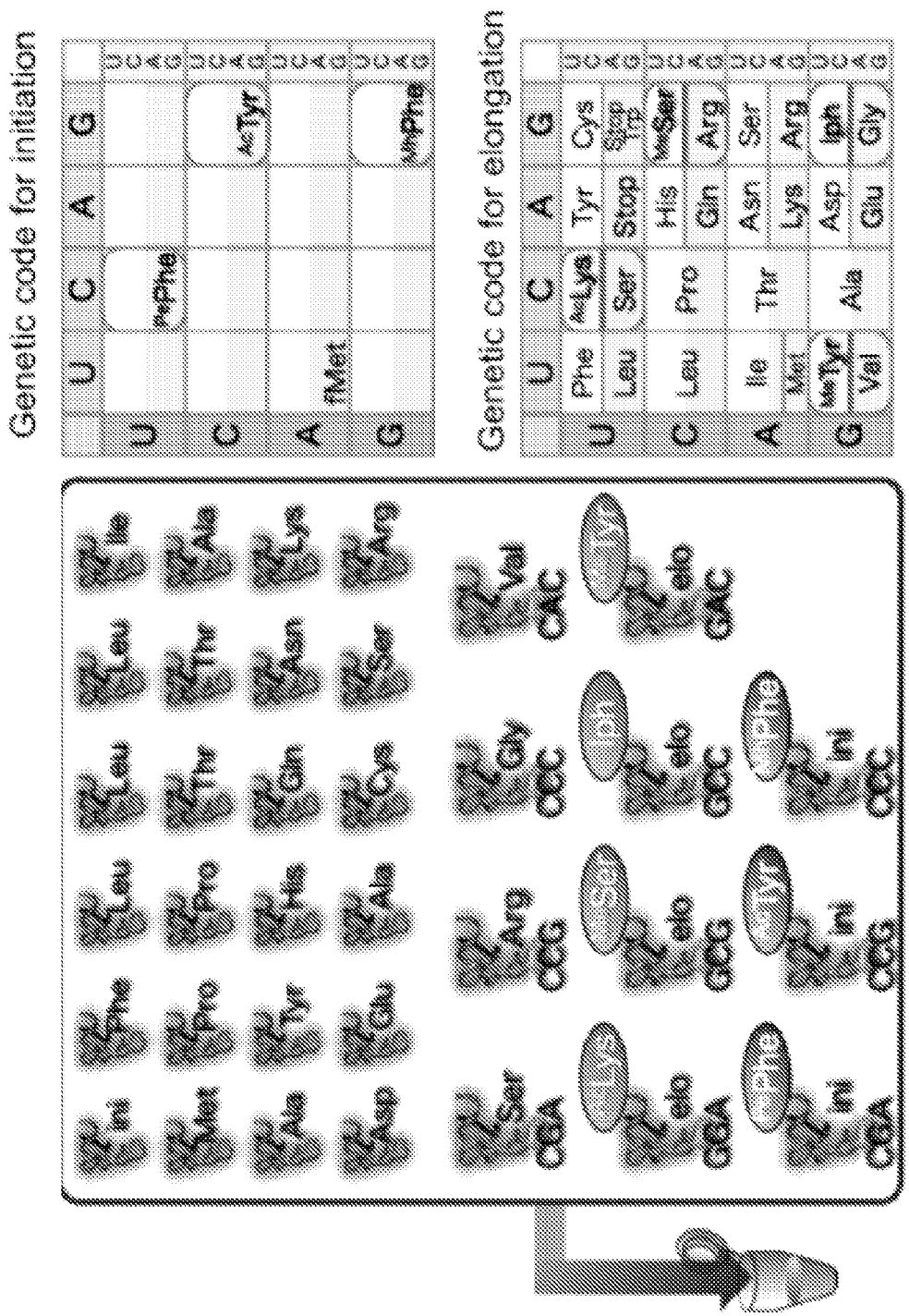

FIG. 11 is a conceptual illustration of the FIT system combining dual genetic codes and divided codon boxes.

Figure 12:
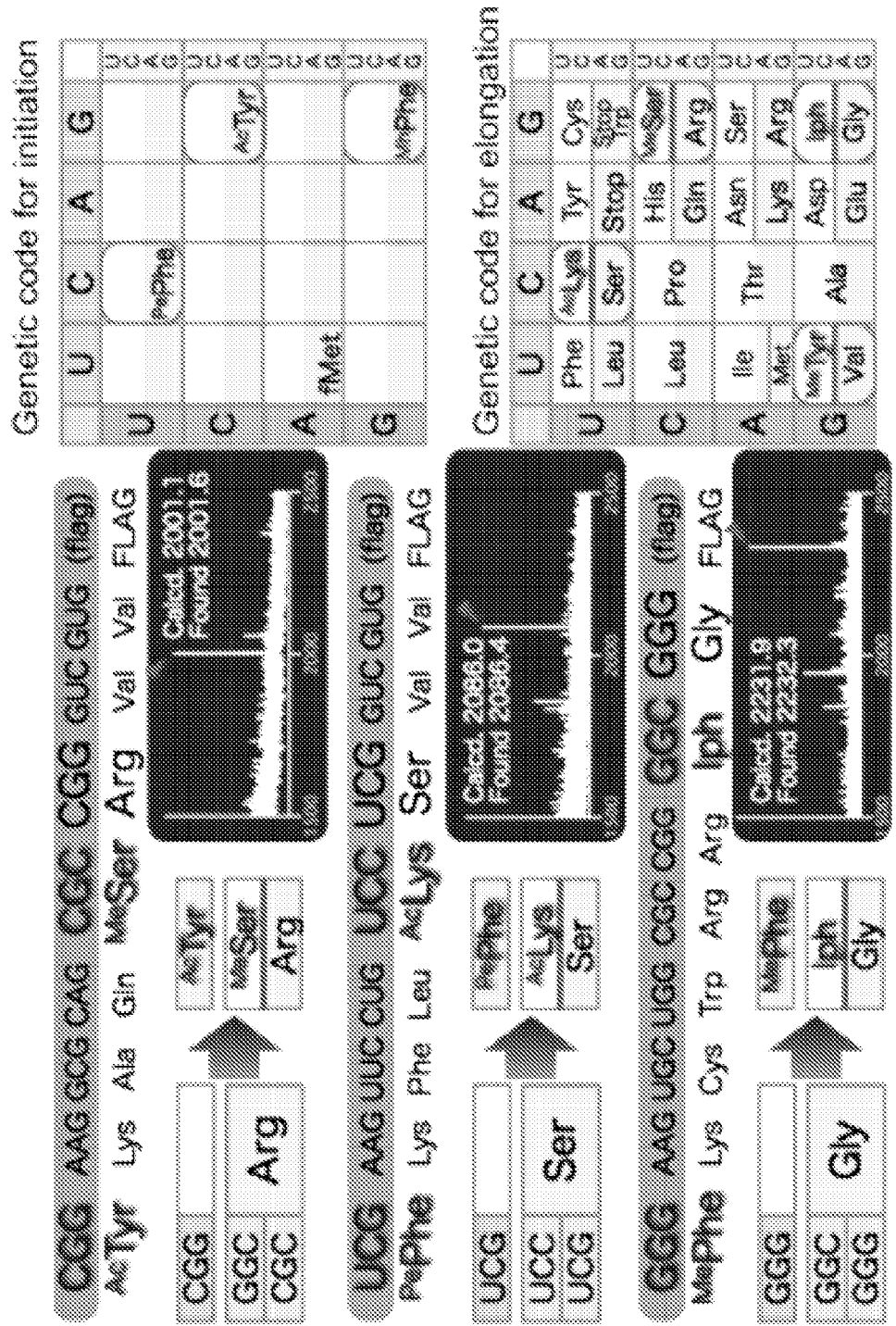

FIG. 12 shows an example of peptide synthesis combining dual genetic codes table and divided codon boxes.

DESCRIPTION OF EMBODIMENTS

Important terms and technology used in the present application will first be described.

"Genetic code (codon)": In the naturally occurring translation, each one of the 20 types of proteinogenic amino acids and translation termination is assigned to each of the 64 types of codons according to the universal genetic code table shown below.

TABLE 1

|   | U |   | C |   | A |   | G |   |   |
|---|---|---|---|---|---|---|---|---|---|
| U | UUU | Phe | UCU | Ser | UAU | Tyr | UGU | Cys | U |
|   | UUC |     | UCC |     | UAC |     | UGC |     | C |
|   | UUA | Leu | UCA |     | UAA | Stop | UGA | Stop | A |
|   | UUG |     | UCG |     | UAG |     | UGG | Trp | G |
| C | CUU | Leu | CCU | Pro | CAU | His | CGU | Arg | U |
|   | CUC |     | CCG |     | CAC |     | CGC |     | C |
|   | CUA |     | CCA |     | CAA | Gln | CGA |     | A |
|   | CUG |     | CCG |     | CAG |     | CGG |     | G |
| A | AUU | Ile | ACU | Thr | AAU | Asn | AGU | Ser | U |
|   | AUC |     | ACC |     | AAC |     | AGC |     | C |
|   | AUA |     | ACA |     | AAA | Lys | AGA | Arg | A |
|   | AUG | Met | ACG |     | AAG |     | AGG |     | G |
| G | GUU | Val | GCU | Ala | GAU | Asp | GGU | Gly | U |
|   | GUC |     | GCC |     | GAC |     | GGC |     | C |
|   | GUA |     | GCA |     | GAA | Glu | GGA |     | A |
|   | GUG |     | GCG |     | GAG |     | GGG |     | G |

The terms, proteinogenic amino acid and natural amino acid, refer to the 20 types of amino acids which are α-amino carbonic acids (or substitutional α-amino carbonic acids) used in normal translation, specifically alanine (Ala), valine (Val), leucine (Leu), isoleucine (Ile), proline (Pro), tryptophan (Trp), phenylalanine (Phe), methionine (Met), glycine (Gly), serine (Ser), threonine (Thr), tyrosine (Tyr), cysteine (Cys), glutamine (Gln), asparagine (Asn), lysine (Lys), arginine (Arg), histidine (His), aspartic acid (Asp), and glutamic acid (Glu).

Figure 1:
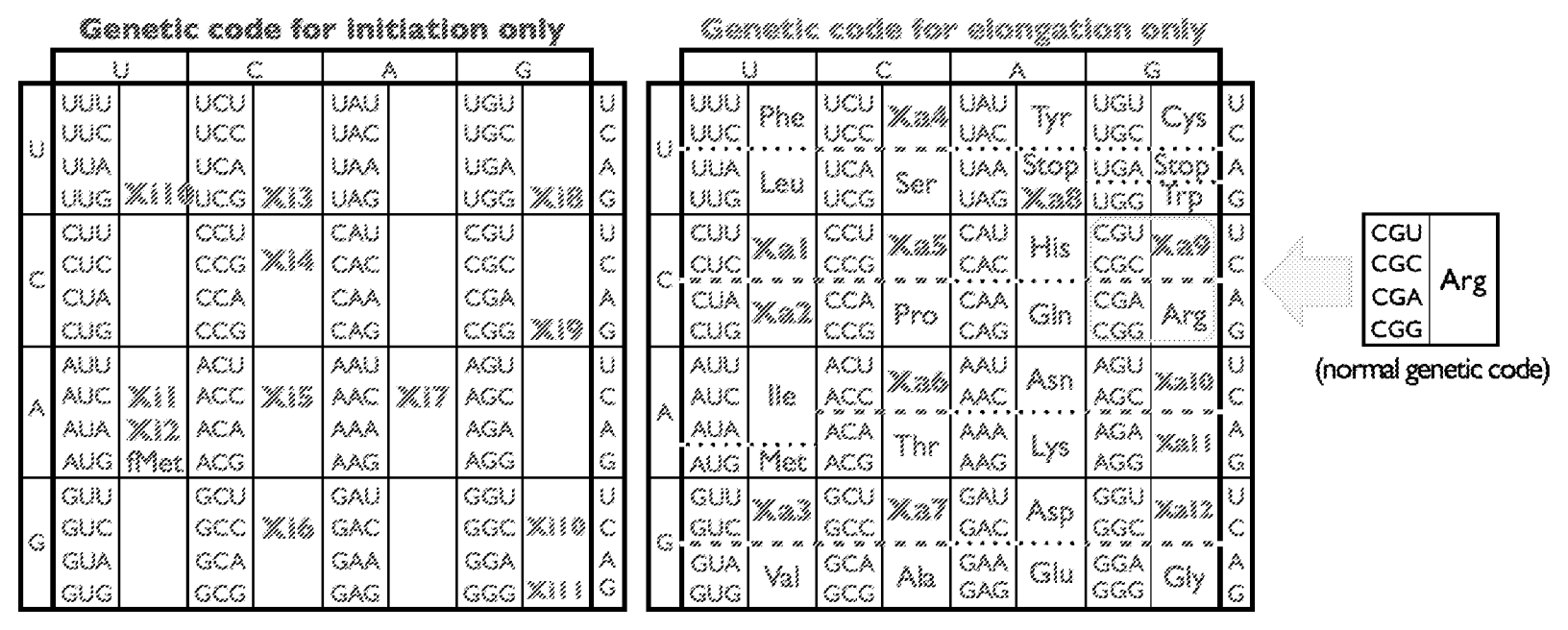

In contrast, in the present invention, the artificial genetic code assigns a special amino acid to each codon. FIG. 1 shows examples of artificial genetic codes presented by the inventors. Two codon tables, one for initiation reaction only (left) and the other for elongation reaction only (right), can be used. Xi and Xa respectively refer to an artificial initiation residue and a special amino acid for elongation.

A codon table for initiation reaction is characterized by the functioning of multiple "artificial initiation codons" that are not AUG.

A codon table for elongation reaction is characterized by the division of the codon boxes enabling additional special amino acids to be defined. There are 11 codon boxes which are not indispensable for the assignment of the 20 proteinogenic amino acids, which are thus divided. Accordingly, a maximum of 11 types of non-standard amino acids can be specified in these codon boxes while maintaining the 20 types of natural amino acids. For example, 2 codons out of 4 or 6 codons each specifying Leu, Val, Ser, Pro, Thr, Ala, Arg, or Gly in the universal genetic code table can remain associated with the original proteinogenic amino acid, while the remaining codons (2 or 4 codons) are reassigned to given special (non-standard) amino acids.

A combination of 2 types of codon tables, one for initiation and the other for elongation, will enable two different amino acids, for the initiation reaction and the elongation reaction, to be defined from a single type of triplet sequence (dual sense codon).

"Special amino acids" and "nonstandard peptides": An amino acid in the present application refers to both a proteinogenic amino acid and a special (i.e., non-standard) amino acid. "Special amino acids" refer, in general, to amino acids that differ in structure from the proteinogenic amino acids used in natural translation. That is, non-proteinogenic amino acids or artificial amino acids, which are proteinogenic amino acids whose side chain structure is chemically changed or modified in part, D-amino acid, N-methyl amino acid, N-acylamino acid, β-amino acid, derivatives having a structure in which the amino group or the carboxyl group on the amino acid backbone is substituted, and the like are all included. For convenience sake, the present specification specifically refers to the special amino acid taken into the N-terminal of peptide in the initiation reaction as "an artificial initiation residue", and in certain cases, a special amino acid taken into the peptide chain during the elongation reaction is referred to as a "special amino acid" in a narrow sense.

"Peptides having special amino acids incorporated therein" or "nonstandard peptides" include polymers whose components include various special amino acids. Nonstandard peptides can have a part or all of the components consisting of special amino acids. Accordingly, nonstandard peptides can have a main chain with a structure differing from a normal amide bond. Examples of nonstandard peptides include depsipeptide constituted from an amino acid and a hydroxyl acid, polyester which is a continuous condensation of hydroxyl acids, N-methyl peptides, and peptides having various acyl groups (e.g. acetyl groups, pyroglutamic acids, fatty acids) on the N-terminal. Nonstandard peptides also include cyclic peptides. As mentioned above, the present inventors had previously developed a means of performing cyclization on a straight chain peptide resulting from translation-synthesis by using an intramolecular reaction and reported it (Goto et al., ACS Chem. Biol., 2008, 3, 120-129, WO 2008/117833 "Synthesis method of cyclic peptide compounds"). The same method can be used in the present application. An example is a cyclic peptide cyclized by a thioether bond, which was obtained by the translation-synthesis of a peptide sequence having a special amino acid comprising a chloroacetyl group positioned on the N-terminal and a cysteine positioned within the peptide chain or on the C terminal. A wide variety of other cyclic structures are possible, other than the above, according to various combinations of functional groups that can be formed by bonding.

A "tRNA" is an RNA molecule having a sequence that can easily form a secondary structure analogous to a structure of a clover. It further has a compact tertiary structure in the shape of L, and functions to bond an amino acid on the 3' terminal on one end of the L-shaped structure (acylation), and to recognize the codon on the mRNA by an anticodon located on the other end. The tRNA in the present specification refers to both a natural tRNA and an artificially constructed tRNA. A typical example of an artificially constructed tRNA is a tRNA synthesized by in vitro transcription.

"Initiator tRNA": A specific tRNA called "initiator tRNA" is necessary to start translation of mRNA. Translation is initiated by the initiator tRNA bonding the initiation amino acid being bonded to a small subunit of ribosome, together with an initiation factor (IF), then the small initiation subunit is bonded to the initiation codon on the mRNA. Since AUG, which is generally a codon of methionine, is used as the initiation codon in the universal code table, an initiator tRNA holds an anticodon corresponding to methionine, and the initiator tRNA always carries methionine (formylmethionine for a prokaryotic cell). However, in the present invention, the initiation amino acid is not limited to methionine and the initiation codon is not limited to AUG, since an initiator tRNA holding an arbitrary anticodon binds an arbitrary initiation amino acid. In the present application, AUG or initiation codons other than AUG that specify amino acids that are not methionine (or formylmethionine) are called "artificial initiation codons". In addition, special amino acids that are specified by artificial initiation codons and incorporated on to the peptide N-terminal are called "artificial initiation residues".

It is said that the first base (first base of the 5' terminal) and the $72^{nd}$ base are mismatched (noncomplementary) in the initiator tRNA of a prokaryote, and the mismatched base pair is taken into the initiation reaction through being recognized by methionylformyltransferase (MTF) and being formylated, and its bond with EF-Tu is restricted (Mayer C, Stortchevoi A, Köhrer C, Varshney U, RajBhandary UL. Initiator tRNA and its role in initiation of protein synthesis. Cold Spring Harb Symp Quasnt Biol. 2001; 66:195-206). It was generally understood concerning the translation initiation reaction derived from a prokaryote that the amino group of the methionine on the initiator tRNA must be modified with a formyl group using formyl group transferase and formyl donors (10-formyl-5,6,7,8-tetrahydroforlic acid). However, a separate research by the present inventors showed that such restriction is unnecessary. Not only can translation be initiated from an amino acid without an acyl group, but an acyl group to be incorporated on to the amino group can have an arbitrary R attached thereto (R—CO-aa-). Hence, a formyl donor and MTF are not necessarily essential in the FIT system.

An example of an initiator tRNA used in the Examples hereinafter is tRNA$^{fMetE}$. The base sequence of the tRNA is based on the natural tRNA$^{fMet}$ of E. coli:
(5'-CGCGGGG$^{s4}$UGGAGCAGCCUGGDAGCUCGUC GGGCmUCAUAACCCGAAGAUCGU CGGTΨCAAAUCCGGCCCCCGCAACCA-3') ($^{s4}$U: 4-thiouridine, D: dihydrouridine, Cm: 2'-O-methylcytidine, T: ribothymidine, pseudouridine) (SEQ ID NO: 7). The underlined section, CAU, is the anticodon, corresponding to the AUG initiation codon.

The present inventors created an initiator tRNA$^{fMetE}$ by in vitro transcription, wherein the initiator tRNA$^{fMetE}$ is the above natural tRNA with the modification base removed and the first C of the 5' terminal changed to G. The sequence of tRNA$^{fMetE}$ used in the Examples of the present application is shown below. The section shown as NNN is the anticodon, and it will be changed to correspond to the initiation codon.
5'-GGCGGGGUGGAGCAGCCUGGUAGCUCGU-CGGGCUNNNAACCCGAAGAUCGUCG GUU-CAAAUCCGGCCCCCGCAACCA-3' (SEQ ID NO: 1)([Sections from which modification was removed, total 6: $^{s4}$U8U, D20U, Cm32C, T54U, Ψ55U.] [Section of mutation, total 1: C1G]).

"Elongator tRNA": An "elongator tRNA" or a "tRNA for elongation" binding an amino acid bonds to an elongation factor Tu (known as EF-Tu in a prokaryote, and eEF-1A in an eukaryote) to be carried to site A on the ribosome. The elongator tRNA of a prokaryote is characterized by the $1^{st}$ base and the $72^{nd}$ base forming a base pair as well as the $50^{th}$ base and the $64^{th}$ base forming a base pair, and the forming of these base pairs are considered necessary in the recognition by EF-Tu.

An example of tRNA for elongation of special amino acids, used in the subsequent Examples, is the artificial tRNA (tRNA$^{AsnE2}$) derived from tRNA$_{Asn}$. The base sequence of the tRNA is based on the natural tRNA$^{Asn}$ of E. coli:
(5'-UCCUCUG$^{s4}$UAGUUCAGDCGGDAGAACGGC GGACUQUU$^{t6}$AAΨCCGUAU$^{m7}$GUCAC UGGTΨCGAGUCCAGUCAGAGGAGCCA-3') ($^{s4}$U: 4-thiouridine, D: dihydrouridine, Q: queuosine, t6A: 6-threonylcarbamoyladenine, Ψ: pseudouridine, m7G: 7-methylguanosine, T: ribothymidine) (SEQ ID NO: 8).

The present inventors used in vitro transcription to prepare a tRNA$^{Asn-E2}$ for elongation that will not be aminoacylated by the 20 types of aminoacylation enzymes of E. coli, removing the modification base from the above natural tRNA and introducing mutation. The section shown as NNN is the anticodon, and it will be changed to correspond to the elongation codon.
(tRNA$^{Asn-E2}$:5'-GGCUCUGUAGUUCAGUCGGUA-GAACGGCGGACUNNNAAUCCGUAUGUCACUG GUUCGAGUCCAGUCAGAGCCGCCA-3' (SEQ ID NO: 2)[Sections from which modification was removed, total 8: $^{s4}$U8U, D16U, D20U, $^{t6}$A37A, Ψ39U, $^{m7}$G46G, T54U, Ψ55U. The $34^{th}$ Q is an anticodon, so it will be changed in accordance with the elongation codon.] [Section of mutation, total 4: U1G, C2G, G71C, A72C]).

"Complementary": A combination of bases of nucleic acids that can form a base pair is referred to as being "complementary" to each other. For a DNA, adenine (A) and thymine (T), and also guanine (G) and cytosine (C) are paired and for an RNA, A and uracil (U), and also, G and C are paired. Further concerning RNAs, a pair like G-U, that is, a non-Watson-Crick base pair, exists as a thermodynamically stable base pair. Hence, the present specification refers to such pair as being "complementary". The relationship between an mRNA codon and a tRNA anticodon depends on the pairing of complementary bases. In particular, a pair that is not a Watson-Crick base pair will be accepted according to the Wobble law in the formation of a complementary chain of the $3^{rd}$ base on the 3' side of codon and the 1st base on the 5' side of codon. When the codon sequence and the anticodon sequence are described as "corresponding", that means that the codon sequence and the anticodon sequence form a complementary chain.

Other methods generally written in various text books and specialized documents are used as materials and methods for working the present invention according to technologies commonly used in the field of chemistry and molecular biology. Specialized documents include a number of articles and patents presented to the public by the present inventors' group.

Method for Translation-Synthesis of Peptides

The present invention relates to a novel in vitro artificial translation-synthesis system "Flexible In-vitro Translation (FIT) system" that is based on a dual genetic code table and an artificial division of codon boxes. Generally speaking, a translation system or a translation-synthesis system is a concept that includes both a process and a kit for the translation-synthesis of peptides.

The method for translation-synthesis of peptides according to the present invention is a method for synthesizing nonstandard peptides by adding a tRNA charged with a special amino acid to an in vitro translation system for peptide synthesis. The "Flexible In-vitro Translation (FIT) system", which is the in vitro translation system mentioned above, is a mixture prepared by mixing protein, RNA, and small molecules required for translation, as necessary. The following technology, which is a system using a ribosome of E. coli, is known as an example of a similar reconstruction-type translation system: H. F. Kung, B. Redfield, B. V. Treadwell, B. Eskin, C. Spears and H. Weissbach (1977) "DNA-directed in vitro synthesis of beta-galactosidase. Studies with purified factors" The Journal of Biological Chemistry Vol. 252, No. 19, 6889-6894; M. C. Gonza, C. Cunningham and R. M. Green (1985) "Isolation and point of action of a factor from Escherichia coli required to reconstruct translation" Proceeding of National Academy of Sciences of the United States of America Vol. 82, 1648-1652; M. Y. Pavlov and M. Ehrenberg (1996) "Rate of translation of natural mRNAs in an optimized in vitro system" Archives of Biochemistry and Biophysics Vol. 328, No. 1, 9-16; Y. Shimizu, A. Inoue, Y. Tomari, T. Suzuki, T. Yokogawa, K. Nishikawa and T. Ueda (2001) "Cell-free translation reconstituted with purified components" Nature Biotechnology Vol. 19, No. 8, 751-755; H. Ohashi, Y. Shimizu, B. W. Ying, and T. Ueda (2007) "Efficient protein selection based on ribosome display system with purified components" Biochemical and Biophysical Research Communications Vol. 352, No. 1, 270-276.

An important feature of the FIT system is that any component of the system can be freely removed. As far as the feature is present in the FIT system, the system allows a component synthesized in vitro to be combined as necessary to a component isolated from an arbitrary organism. The description in the present specification and the Examples hereinafter refer to a system derived from prokaryote for explanation, and only for the sake of explanation, so there is no intention to exclude the use of a translation system derived from eukaryote.

The present invention is described below in line with the Examples using ribosome derived from E. coli.

Typical compositions of a translation system conventionally included (i) T7 RNA polymerase (when accompanied by transcription from DNA), (ii) initiation factor, elongation factor, termination factor, ribosome recycling factor of E. coli, as translation factors, (iii) 20 types of aminoacyl tRNA synthetase (ARS), methionyl tRNA formyl transferase (MTF), (iv) E. coli 70S ribosome, (v) E. coli tRNA (isolated from E. coli), (vi) various amino acids, NTP, energy regeneration system and others.

All or part of the ingredients of the above (ii) and (iii) and (v) are not included in the FIT system used in the present invention. For example, a translation system is prepared, excluding component molecules such as amino acid, aminoacyl tRNA synthetase, methionyl tRNA formyl transferase, termination factor, and tRNA. Such a system will stop functioning as a normal translation system, but adding artificially synthesized factors such as a tRNA resulting from in vitro transcription-synthesis and charged with an amino acid and other components will revive the peptide synthesis function. In other words, reprogramming of desired genetic codes is possible by excluding components of the translation system, as necessary.

The aminoacyl tRNA, which is necessary for assigning special amino acids and artificial initiation residues, is prepared by isolating tRNA resulting from in vitro transcription-synthesis and subjecting it to in vitro aminoacylation. To aminoacylate isolated tRNA in vitro is to bond the desired amino acid to the 3' terminal of tRNA under a condition devoid of other tRNA and ARS. Such aminoacylation should preferably be a method that is applicable to any amino acid, since the special amino acids and artificial initiation residues to be incorporated into the peptide is unrestricted in the present invention. A chemical aminoacylation method (Heckler T. G., Chang L. H., Zama Y., Naka T., Chorghade M. S., Hecht S. M.: T4 RNA ligase mediated preparation of novel "chemically misacylated" tRNAPheS. Biochemistry 1984, 23:1468-1473) and a method using an aminoacyl tRNA synthesis ribozymes (ARS ribozymes) developed by the present inventors are examples of methods known in the art. Another available method is a method using enzymes that are artificially altered from natural ARS, although it is limited in the types of amino acids that it can be applied to.

In the present invention, the most preferable method for in vitro aminoacylation of tRNA is a synthesis method using tRNA resulting from in vitro transcription-synthesis as the substrate and using ARS ribozymes.

An aminoacyl tRNA synthetase that is preferable for use in the present invention is ARS ribozyme (flexizyme), which is an RNA catalyst produced using molecular evolution engineering by the present inventors. ARS ribozymes differ from natural ARS protein enzymes in that they are not specific to an amino acid or a tRNA, and they can perform aminoacylation by using any amino acid or hydroxy acid which falls outside cognate amino acids originally designated for charging.

A flexizyme is also known by the names, dinnitrobenzyl flexizyme (dFx), enhanced flexizyme (eFx), and aminoflexizyme (aFx). The use of these ARS ribozymes enables any tRNA to bind desired artificial initiation residues or special amino acids.

Examples of known ARS ribozymes (RNA sequences) are shown below.

```
A prototype flexizyme Fx
                                                (SEQ ID NO: 3)
[GGAUCGAAAGAUUUCCGCAGGCCCGAAAGGGUAUUGGCGUUAGGU-3', 45 nt];

Dinitrobenzyl flexizyme dFx
                                                (SEQ ID NO: 4)
[5'-

GGAUCGAAAGAUUUCCGCAUCCCCGAAAGGGUACAUGGCGUUAGGU-3', 46 nt];

Enhanced flexizyme eFx
                                                (SEQ ID NO: 5)
[5'-

GGAUCGAAAGAUUUCCGCGGCCCCGAAAGGGGAUUAGCGUUAGGU-3', 45 nt]);

Aminoflexizyme aFx
                                                (SEQ ID NO: 6)
[5'-

GGAUCGAAAGAUUUCCGCACCCCCGAAAGGGGUAAGUGGCGUUAGGU-

3', 47 nt]).
```

The aminoacylation reaction by flexizymes can be conducted under mild conditions, and the flexizymes can be incorporated into the translation system after a simple after-treatment. Flexizymes have catalytic abilities of recognizing a carbonyl group, which is a reaction point of amino acid, and an aromatic ring which is a side chain or a leaving group of amino acid, and the 5'-RCC-3' sequence section (R=A or G) on the 3' terminal of tRNA and aminoacylating an amino acid to adenosine on the 3' terminal. The aminoacylation catalyzed by flexizymes progresses just by placing the amino acid substrate and the object it bonds to, namely the tRNA molecule, on ice for about 2 hours under the presence of flexizyme. Refer to the following references for details. H. Murakami, H. Saito, and H. Suga, (2003), Chemistry & Biology, Vol. 10, 655-662; H. Murakami, D. Kourouklis, and H. Suga, (2003), Chemistry & Biology, Vol. 10, 1077-1084; H. Murakami, A. Ohta, H. Ashigai, H. Suga (2006) Nature Methods 3, 357-359 "A highly flexible tRNA acylation method for non-natural polypeptide synthesis"; N. Niwa, Y. Yamagishi, H. Murakami, H. Suga (2009) Bioorganic & Medicinal Chemistry Letters 19, 3892-3894 "A flexizyme that selectively charges amino acids activated by a water-friendly leaving group"; and WO 2007/066627.

In the present invention, artificial tRNA that becomes orthogonal to natural ARS is used as elongator tRNA for special amino acids. That is, the present invention uses an artificial tRNA that will not be recognized by natural ARS inherent in the translation mixture and that will not be charged by natural amino acids in the translation system. Such artificial tRNA may be synthesized through in vitro transcription. Artificial tRNA (tRNA$^{AsnE2}$) derived from *E. coli* tRNA$_{Asn}$ is used in the following explanation and Examples as an example of tRNA for elongation of special amino acids. However, any tRNA that becomes orthogonal to inherent ARS in the translation system and whose use in an elongation reaction of peptide on ribosome has been confirmed can be used without being limited by the above example.

An initiator tRNA has a different sequence from an elongator tRNA, and is recognized by an initiation factor. An artificial tRNA (tRNA$^{fMetE}$) derived from *E. coli* tRNA$^{fMet}$, which is synthesized through in vitro transcription, is used in the subsequent Examples. However, any tRNA can be used without being limited by the above example, if it has been confirmed in the subject translation system as being usable in an initiation reaction of peptide translation on ribosome.

Components of Fit System

A kit containing specific components for the translation-synthesis of nonstandard peptides is another aspect of the present invention. Specific components of the translation system that can be used in the present invention are explained below by comparison with conventionally known systems.

A translation mixture is provided with a DNA or RNA molecule that corresponds to a base sequence that acts as a template for translation. A suitable RNA polymerase, such as T7 RNA polymerase, is added to perform transcription from a template DNA. RNA polymerase is not necessary when adding a transcribed mRNA to the translation system. A nucleic acid sequence can include additional base sequences that are advantageous for translation according to the subject translation system, in addition to the region for encoding the target amino acid sequence, similar to protein expression systems using living cells. In case of an system using ribosome derived from *E. coli*, the efficiency of translation reaction will increase if it includes a Shine-Dalgarno (SD) sequence or an epsilon sequence upstream of the initiation codon. There is no difference from conventional in vitro translation systems so far. Placed on the N-terminal in the region encoding a peptide is an artificial initiation codon that specifies a special amino acid that acts as an artificial initiation residue. Special amino acids that are incorporated in the elongation reaction are specified by elongation codons. Sequences for connecting the nucleic acid molecule and peptide, which is its translation product, may be included on the C terminal side for in vitro display, similar to conventional systems.

Further, the translation mixture is provided with tRNAs that have been aminoacylated in advance with artificial initiation residues or special amino acids, for artificial initiation residues and special amino acids. A set including proteinogenic amino acid, tRNA, and a specific ARS protein enzyme is provided for proteinogenic amino acids. In conventionally known systems using ribosome of *E. coli*, tRNA derived from *E. coli* is used as the tRNA for proteinogenic amino acids, but an artificial tRNA synthesized through in vitro transcription is used in the present invention. Concerning ARS, 20 types of ARS corresponding to all proteinogenic amino acids are used in conventionally known systems, but the present invention does not necessarily require all 20 types of ARS, since dual genetic codes and divided genetic codes specified as necessary are used.

In contrast to the normal translation reaction requiring a formyl donor, such as 10-formyl-5,6,7,8-tetrahydroforlic acid (Baggott et al., 1995), as a mandatory component, due to N-formylmethionine being associated to the initiation codon AUG by the initiator tRNA, a formyl donor is optional in the present invention, since the initiation codon AUG or the artificial initiation codon is used to incorporate special amino acids (artificial initiation residues) in the present invention. Methionyl-tRNA formyltransferase (MTF) is also optional for the same reason.

The ribosome is mandatory as a protein synthesis machine, as in conventional systems. The ribosome is an RNA-protein complex of 50 or more types of ribosome proteins and a few types of RNA molecules (rRNA) gathered together, which reads out genetic information of mRNA and catalyzes the polymerization of amino acids. Ribosomes isolated from *E. coli* are preferably used, but ribosomes derived from other organisms can also be used.

In addition, translation initiation factors (e.g. IF1, IF2, IF3), translation elongation factors (e.g. EF-Tu, EF-Ts, EF-G), translation termination factors (e.g. RF1, RF2, RF3, RRF) and enzymes for energy source regeneration (e.g. creatine kinase, myokinase, pyrophosphatase, nucleotide-diphosphatase kinase) are used for proteins, of which the translation termination factors and the enzymes for energy source regeneration are added by option.

Further, appropriate buffers, NTPs as the energy source of translation reaction, Creatine phosphate, and factors necessary for ribosome activation, RNA stabilization, protein stabilization and others can be used as necessary.

Furthermore, enzymes, such as peptide deformylase (PDF) and methionine aminopeptidase (MAP), that do not directly participate in the translation reaction can be additionally added as necessary to synthesize peptides comprising a cyclized main chain, as verified in another research by the present inventors (T. Kawakami, A. Ohta, M. Ohuchi, H. Ashigai, H. Murakami, H. Suga, Nat. Chem. Biol., 2009, 5, 888-890).

The invention is described below with artificial initiation residues represented by Xi and special amino acids used in the elongation reaction represented by Xa.

1. Dual Genetic Code

Aminoacyl initiator tRNAs with various anticodon sequences are added to the translation mixture to enable multiple codons to be used as artificial initiation codons. Each tRNA can be charged with a different artificial initiation residue so that a corresponding artificial initiation residue will be assigned to the codon (artificial initiation codon) corresponding to the anticodon sequence. When sequences for artificial initiation codons exist at the positions for initiation codons on the mRNAs to be translated, the corresponding aminoacyl initiator tRNAs (e.g. an aminoacyl tRNA$^{fMetE}$ possessing a corresponding anticodon sequence) read out those sequences to synthesize peptides with desired artificial initiation residues on the N-terminal.

Aminoacyl elongator tRNAs with various anticodon sequences (e.g. an aminoacyl tRNA$^{AsnE2}$ possessing a corresponding anticodon sequence) are added to the translation mixture so that the artificial initiation codon sequences used above can also be utilized in the elongation reaction as dual sense codons.

The initiator tRNA and the elongator tRNA will not function to take the place of the other by mistake (e.g. the elongator tRNA is not used in the initiation reaction, nor is the initiator tRNA used in the elongation reaction). This enables different amino acids to be assigned to the codon sequence for the initiation reaction and for the elongation reaction.

2. Artificial Division of the Codon Box

Natural tRNAs can read out the sequences of all 4 codons in one codon box by 3 or less tRNAs, since natural tRNAs are modified in the base sequence. For example, a tRNA corresponding to Val and consisting of an anticodon sequence UAC whose U is modified to cmo5U reads out all 4 codons of GU(U/C/A/G). That is why the GUN codon box is occupied by Val.

To prevent such mismatch between codon-anticodon sequences from being accepted, the artificial division of codon boxes is performed using only artificially synthesized tRNAs that include no modified base, and absolutely no natural tRNA. Those which are synthesized in vitro by suitable RNA polymerases are preferable. Such tRNAs, resulting from in vitro synthesis, do not read out 4 types of codons as described above, since the tRNAs include no modified base.

The codon box of Val is used as an example for explanation. In it, tRNA$^{Val}_{CAC}$ containing a CAC anticodon resulting from in vitro synthesis and tRNA$^{AsnE2}$(Xa-tRNA$^{AsnE2}_{GAC}$) acylated by a desired special amino acid and containing a GAC anticodon were added. Consequently, the tRNA$^{val}_{CAC}$ is converted in the system to Val-tRNA$^{val}_{CAC}$ by the ARS of Val and reads out the GUG codon to assign Val. At the same time, the Xa-tRNA$^{AsnE2}_{GAC}$ separately assigns Xa by reading out the GU(U/C) codon. Such process allows the codon box, normally used only for a single amino acid, to be artificially divided, so that desired special amino acids can be added to the genetic code while maintaining the original proteinogenic amino acids.

The present invention is described in detail by the Examples below. The Examples are for explaining the patent, and they do not limit the scope of the present invention.

Example 1

Experiment confirming that multiple codons other than AUG function as artificial initiation codons (FIG. 3).

Multiple mRNAs with various codons positioned on the initiation codon sites (mRNA1$_{XXX}$, wherein XXX stands for the sequence of artificial initiation codon positioned on respective mRNAs) were prepared.

The mRNAs were translated under the presence of tRNAs ($^{Ac}$Phe-tRNA$^{fMetE}_{xxx}$, wherein xxx stands for respective anticodons), which are tRNA$^{fMetE}$ charged with N-acetylphenyl alanine ($^{Ac}$Phe) when tRNA$^{fMetE}$ holds an anticodon corresponding to the respective artificial initiation codon sequences, to confirm whether peptides with $^{Ac}$Phe on desirable N-terminals are obtained as translation products.

It was consequently shown that the translation reaction can be started with at least UGG, AUC, ACC, UCG, AAC, GCC, GGC, CCG, CGG, AUA, in addition to the natural initiation codon, AUG, and that a wide variety of codons can be used as artificial initiation codons.

Example 2

Experiment confirming that the same codon functions in both initiation and elongation, and codes for different amino acids (FIG. 4)

Multiple mRNAs with various codons positioned on both the initiation codon site and the elongation codon site (mRNA2$_{XXX}$, wherein XXX stands for the dual sense codon sequence to be assessed, which is positioned on the mRNA) were prepared. tRNAs were prepared, specifically, tRNAs composed of tRNA$^{fMetE}$ charged with N-acetylphenyl alanine ($^{Ac}$Phe) ($^{Ac}$Phe-tRNA$^{fMetE}_{xxx}$, wherein xxx stands for the respective anticodons), wherein a tRNA$^{fMetE}$ contains anticodon sequences corresponding to the dual sense codon sequences, and tRNAs composed of tRNA$^{AsnE2}$ having the same anticodon sequence charged with N-acetyllycine (Aly) (Aly-tRNA$^{AsnE2}_{xxx}$). The mRNAs were translated under the presence of the 2 types of aminoacyl tRNAs to confirm whether peptides with $^{Ac}$Phe on the desired N-terminal and Aly in the peptide chains were obtained as translation products.

It was consequently confirmed that at least AUG, UGG, AUC, ACC, UCG, AAC codons function as dual sense codons, and specify different amino acids in each of the initiation reaction and the elongation reaction.

Example 3

Experiment of using a dual genetic code to simultaneously use a total of 8 types of special amino acids and artificial initiation residues (FIG. 5)

The dual genetic code used in the test was arranged with 4 types of artificial initiation residues, namely N-acetylphenyl alanine ($^{Ac}$Phe), N-pentenoylphenyl alanine ($^{Pe}$Phe), N-aminomethylbenzoylphenyl alanine ($^{BA}$Phe), N-methylhexanoylphenyl alanine ($^{Mh}$Phe), respectively positioned on the artificial initiation codons of AUG, UCG, AAC, UGG, and 4 types of special amino acids, namely N-acetyllycine (Aly), iodopheyl alanine (Iph), hydroxyproline (Hyp), citrulline (Cit) respectively positioned on the elongation codons of AUG, UCG, AAC, UGG. Eight types of aminoacyl tRNAs, namely $^{Ac}$Phe-tRNA$^{fMetE}_{CAU}$, $^{Pe}$Phe-tRNA$^{fMetE}_{CGA}$, $^{BA}$Phe-tRNA$^{fMetE}_{GUU}$, $^{Mh}$Phe-tRNA$^{fMetE}_{CCA}$, Aly-tRNA$^{AsnE2}_{CAU}$, Iph-tRNA$^{AsnE2}_{CGA}$, Hyp-tRNA$^{AsnE2}_{GUU}$, Cit-tRNA$^{AsnE2}_{CCA}$, were consequently prepared and added to the translation system. Additionally, 4 types of mRNA (mRNA2$_{AUG}$, mRNA2$_{UGG}$, mRNA2$_{AAC}$, mRNA2$_{UGG}$) were mixed to be coexpressed in a single translation system.

In the resulting translation product mixture were only the 4 desired types of peptides. The result showed that multiple peptides with different N-terminals (artificial initiation residues) and special amino acids can be mixed and synthesized by a single reaction when a translation system based on the dual genetic code is used.

Example 4

Experiment confirming that tRNA, resulting from in vitro transcription-synthesis using T7 RNA polymerase, functions in a translation reaction (FIG. 6)

Multiple mRNA4$_{XXX}$ (wherein, XXX is one of various codons), each comprising a codon that codes for one of the 20 types of proteinogenic amino acids, were prepared, and the mRNAs were expressed in a translation system comprising only those tRNAs which were prepared by in vitro transcription-synthesis (i.e. translation system without natural tRNAs).

Peptides comprising all types of amino acids were synthesized as a result. It was thus confirmed that translation-synthesis functions as normal even if the tRNA used is tRNA resulting from in vitro transcription-synthesis by T7 RNA polymerase.

Example 5

Experiment of artificially dividing codon boxes (FIG. 7-10)

An experiment of artificially dividing the codon boxes of valine, serine, arginine, and glycine is described hereinafter.

FIG. 7 is a conceptual illustration of the codon box division experiment. The test uses a translation system without natural tRNAs. Added to the system are tRNA required for specifying 20 types of proteinogenic amino acids (synthesized by in vitro transcription) and an aminoacyl tRNA required for specifying the desired special amino acid (synthesized by in vitro transcription and the acylation technology using flexizyme, etc.). The addition of tRNAs induces the artificial division of codon boxes resulting in the co-existence of an original proteinogenic amino acid and a special amino acid in each divided box.

A translation system was prepared, the system having added thereto in vitro transcribed tRNAs (tRNA$^{Val}_{CAC}$, tRNA$^{Arg}_{CCG}$, tRNA$^{Ser}_{CGA}$, tRNA$^{Gly}_{CCC}$) to code for the 4 types of amino acids positioned at the divided codons, in vitro transcribed tRNAs for the other 16 types of proteinogenic amino acids, and tRNA$^{AsnE2}$ ($^{Me}$Tyr-tRNA$^{AsnE2}_{GAC}$, $^{Me}$Ser-tRNA$^{AsnE2}$, Aly-tRNA$^{AsnE2}_{GGA}$, Iph-tRNA$^{AsnE2}_{GCC}$) charged with 4 respective types of special amino acids. The genetic codes used in the translation system are characterized by each of the 4 codon boxes above being artificially divided and enabling an original proteinogenic amino acid and a special amino acid to co-exist.

As a result of expressing various sequences of mRNA by using the above translation system, desired peptides were obtained for all cases (i.e. peptides including both the natural and artificial amino acids that exist in the divided codon boxes). The concept of the artificial division of codon boxes was thus proven experimentally. Concurrently, a translation-synthesis system that enables the simultaneous use of the 20 types of natural amino acids and the 4 types of special amino acids was established.

FIGS. 8 to 10 are exemplary experiment results for codon box division.

In FIG. 8, the codon box of GUN is divided with a proteinogenic amino acid Val assigned to the GUG codon and the special amino acid $^{Me}$Tyr assigned to the GUC codon.

[Upper column] The mRNA sequence that was used and the amino acid sequence coded for by the mRNA sequence (P-1 and P-2).

[Lower column] A translation product, Tricine-SDS PAGE. Lane 1: mRNA was translated by a normal translation system containing all natural tRNAs to synthesize P-1. Lane 2: mRNA was translated by a translation system containing necessary in vitro transcribed tRNA, without any natural tRNA included therein, to synthesize P-1. Lane 3: mRNA was translated by a translation system containing necessary in vitro transcribed tRNA and an artificial aminoacyl tRNA, without any natural tRNA included therein, to synthesize P-2.

[Lower column/right] The mass analysis result of peptides obtained by translation-synthesis under the conditions of Lanes 2 and 3 of the Tricine-SDS PAGE.

Synthesis of peptides with the sequences of P-1 and P-2, as specified, was confirmed.

In FIG. 9, the codon boxes of (1) CGN, (2) UCN, (3) GGN were divided and (1) $^{Me}$Ser, (2) Aly, (3) Iph were respectively assigned to the codon boxes as special amino acids. In addition, the mass analysis result of peptides obtained by the translation-synthesis using the divided genetic codes is shown on the right. Synthesis of peptides containing both the natural and artificial amino acids in the divided codon boxes, as specified by the divided genetic codes, was confirmed.

FIG. 10 shows an experiment in which 2 codon boxes are divided with one effort.

The following codon boxes were divided: (1) CGN, GUN, (2) UCN, GUN, (3) CGN, GGN. The result of mass analysis of the translation product after actually conducting translation-synthesis is shown on the right. Synthesis of peptides containing both the natural and artificial amino acids in the divided codon boxes, as specified by the divided genetic codes, was confirmed.

Example 6

New artificial translation-synthesis system that combines dual genetic code table and artificial codon box division (FIGS. 11-12)

FIG. 11 is a conceptual illustration of a new artificial translation system that combines a dual genetic code table and divided codon boxes. The translation system uses a translation system without any natural tRNAs. Added to the system are tRNAs required for specifying 20 types of proteinogenic amino acids (synthesized by in vitro transcription) and aminoacyl tRNAs required for specifying the desired special amino acids (synthesized by in vitro transcription and the acylation technology using flexizyme, etc.). The addition of the tRNAs results in an increase of the types of initiation codons that can be used and causes an artificial initiation residue to be assigned to each initiation codon. Meanwhile, in the elongation reaction, the addition induces the artificial division of the codon boxes and results in the co-existence of an original proteinogenic amino acid and a special amino acid in each divided box.

The present Example divides the codon boxes of serine, arginine, glycine artificially. Specific codons in the boxes are not only used as artificial initiation codons but also function as dual sense codons.

A translation system was prepared, the system having added thereto in vitro transcribed tRNA$^{fMetE}$ charged with one of the 3 types of artificial initiation residues ($^{Ac}$Tyr-tRNA$^{fMetE}_{CCG}$, $^{Pen}$Tyr-tRNA$^{fMetE}_{CGA}$, $^{Mh}$Phe-tRNA$^{fMetE}_{CCC}$), tRNA$^{AsnE2}$ charged with one of the 3 types of special amino acids ($^{Me}$Ser-tRNA$^{AsnE2}_{GCG}$, Aly-tRNA$^{AsnE2}_{GGA}$, Iph-tRNA$^{AsnE2}_{GCC}$), in vitro transcribed tRNA to code for one of the 3 types of amino acids positioned at the divided codons (tRNA$^{Arg}_{CCG}$, tRNA$^{Ser}_{CGA}$, tRNA$^{Gly}_{CCC}$), in vitro transcribed tRNAs for the other 17 types of proteinogenic amino acids. The genetic codes used in the translation system are characterized by the 3 codon boxes above which are each artificially divided and the dual sense codons placed therein, which function in both initiation and elongation, enabling an original proteinogenic amino acid, an artificial initiation residue and a special amino acid to co-exist in a single codon box.

FIG. 12 shows the result of the above example of peptide synthesis. The codon boxes of (1) CGG, (2) UCG, (3) GGG were used herein as artificial initiation codons; in the elongation reaction, the codon boxes of (1) CGN, (2) UCN, (3) GGN were divided to have special amino acids assigned thereto. As a result of a mass analysis of the translation product after actually conducting the translation-synthesis, synthesis of peptides was confirmed, in which the peptides contain both the natural and artificial amino acids in the codon boxes and have an artificial initiation residue on the N-terminal, as specified by the dual genetic codes that include divided codons.

As a result of expressing various sequences of mRNAs by using the above translation system, desired peptides were obtained for all cases (i.e. peptides including both the artificial initiation residues, and natural and artificial amino acids specified in the divided codon boxes). The combination of dual genetic codes and an artificial division of codon boxes was thus experimentally proven possible. Concurrently, a translation-synthesis system that enables the simultaneous use of the 20 types of natural amino acids, the 3 types of artificial initiation residues and the 4 types of special amino acids was established.

INDUSTRIAL APPLICABILITY

The present inventors have developed translation-synthesis methods for peptides with various special backbones (nonstandard peptides) by utilizing specific special amino acids in the translation system. Nonstandard peptide is a generic name of peptides that include the structures of an N-terminal acyl group, an N-methyl amino acid, a D-amino acid, and a macrocyclic backbone. Since it includes these special backbones, it is provided with properties necessary for medicines, such as membrane permeability, specificity, and biological stability, and it is promising as a motif for developing medicines. Since translation systems are good synthesis methods for constructing a peptide library, the technology that allows nonstandard peptides to be synthesized in translation apparatuses is increasingly appreciated as an extremely competent tool for searching for new candidates of medicine.

The number of special amino acids that can be used in a single translation system can be increased by the present technology (20 types or more of special amino acids can be added to the common 20 types of proteinogenic amino acids to achieve 40 types or more). The increase greatly expands the sequence space of nonstandard peptide libraries constructed by the translation system. This indicates that the obtained peptide library will have not only a high diversity in sequence but also a high diversity in structure, and consequently, a library of a higher quality can be constructed.

SEQUENCE LISTING FREE TEXT

SEQ ID NO: 1 tRNA$^{fMetE}$
SEQ ID NO: 2 tRNA$^{Asn-E2}$
SEQ ID NO: 3 Fx
SEQ ID NO: 4 dFx
SEQ ID NO: 5 eFx
SEQ ID NO: 6 aFx
SEQ ID NO: 7 tRNA$^{fMet}$
SEQ ID NO: 8 tRNA$^{Asn}$

---

The invention claimed is:

1. A method for synthesizing peptides using dual sense codons and artificial division of codon boxes, comprising:
   i) combining at least the following in an in vitro translation system:
      (a) mRNAs;
      (b) initiator tRNA(s) each charged with a (b) artificial amino acid;
      (c) elongator tRNA(s) each charged with a (c) natural amino acid, wherein each of the (c) tRNA(s) is independently complementary to first codon(s) of the mRNA of its (c) natural amino acid in the genetic code;
      (d) elongator tRNA(s) each charged with a (d) artificial amino acid, wherein at least one of the (d) tRNA(s) is independently complementary to second codon(s) of the mRNA of an (c) natural amino acid in the genetic code;
      (e) optionally, initiator tRNA(s) and/or elongator tRNA(s) each charged with a natural or an artificial amino acid,
      wherein a codon for each (b) initiator tRNA is the same as a codon for a (c) elongator tRNA or a (d) elongator tRNA; and
   ii) synthesizing at least one peptide comprising a (b) artificial amino acid, a (c) natural amino and a (d) artificial amino acid using the mRNAs and tRNA(s) in the in vitro translation system,
   wherein a codon for a (b) initiator tRNA of the (b) artificial amino acid is the same as a codon for a (c) elongator tRNA of the (c) natural amino acid or a codon for a (d) elongator tRNA of the (d) artificial amino acid, and
   wherein the (b) artificial amino acid and the (d) artificial amino acid in the at least one peptide are different if the codon for the (b) initiator tRNA is the same as the codon for the (d) elongator tRNA.

2. The method according to claim 1, wherein the (b) initiator tRNA(s) each charged with a (b) artificial amino acid and (d) elongator tRNA(s) each charged with a (d) artificial amino acid are prepared by an in vitro aminoacylation of tRNAs formed by in vitro transcription.

3. The method according to claim 1, wherein the
(c) natural amino acid is one or more selected from Leu, Val, Ser, Pro, Thr, Ala, Arg, and Gly.

4. The method according to claim 3, wherein a codon for a (e) elongator tRNA charged with an (e) artificial amino acid may be a termination codon selected from UAG, UAA and UGA.

5. The method according to claim 1 or 2, wherein the translation system comprises in vitro transcribed tRNAs that are capable of being charged with the natural amino acids by the catalysis of endogenous ARSs.

6. The method according to claim 1 or 2, wherein the codon assigning the translation initiation is AUG.

7. The method according to claim 1 or 2, wherein codon(s) for (b) initiator tRNA(s) are selected from AUG, UGG, AUC, ACC, UCG, AAC, GCC, GGC, CCG, CGG, GGG, and AUA.

8. The method according to claim 6, wherein AUG is a codon for a (d) elongator tRNA charged with an (d) artificial amino acid.

9. The method according to claim 7, wherein codon(s) for (b) initiator tRNA(s) are selected from AUG, UGG, AUC, ACC, UCG and ACC.

10. A kit for an in vitro translation system that expresses a nonstandard peptide using dual sense codons and artificial division of codon boxes, comprising at least:
    (a) a ribosome
    (b) initiator tRNA(s) each charged with a (b) artificial amino acid;
    (c) elongator tRNA(s) each charged with a (c) natural amino acid, wherein each of the (c) tRNA(s) is independently complementary to first codon(s) of the mRNA of its (c) natural amino acid in the genetic code;
    (d) elongator tRNA(s) each charged with a (d) artificial amino acid, wherein at least one of the (d) tRNA(s) is independently complementary to second codon(s) of the mRNA of an (c) natural amino acid in the genetic code,
    (e) optionally, initiator tRNA(s) and/or elongator tRNA(s) each charged with a natural or an artificial amino acid,
    wherein a codon for each (b) initiator tRNA is the same as a codon for a (c) elongator tRNA or a (d) elongator tRNA.

11. The method according to claim 1 or 2, wherein a codon for a (b) initiator tRNA can be selected from any triplet sequence.

* * * * *

SEQUENCE LISTING

```
<160> NUMBER OF SEQ ID NOS: 8

<210> SEQ ID NO 1
<211> LENGTH: 77
<212> TYPE: RNA
<213> ORGANISM: Artificial
<220> FEATURE:
<223> OTHER INFORMATION: Synthetic oligonucleotide: tRNAfMetE
<220> FEATURE:
<221> NAME/KEY: misc_feature
<222> LOCATION: (35)..(37)
<223> OTHER INFORMATION: n stands for any base

<400> SEQUENCE: 1 ggcgggugg agcagccugg uagcucgucg ggcunnnaac ccgaagaucg ucgguucaaa      60
uccggccccc gcaacca                                                    77

<210> SEQ ID NO 2
<211> LENGTH: 76
<212> TYPE: RNA
<213> ORGANISM: Artificial
<220> FEATURE:
<223> OTHER INFORMATION: Synthetic oligonucleotide: tRNAAsn-E2
<220> FEATURE:
<221> NAME/KEY: misc_feature
<222> LOCATION: (34)..(36)
<223> OTHER INFORMATION: n stands for any base

<400> SEQUENCE: 2
ggcucuguag uucagucggu agaacggcgg acunnnaauc cguaugucac ugguucgagu      60
ccagucagag ccgcca                                                     76
```

```
<210> SEQ ID NO 3
<211> LENGTH: 45
<212> TYPE: RNA
<213> ORGANISM: Artificial
<220> FEATURE:
<223> OTHER INFORMATION: Synthetic oligonucleotide: Fx

<400> SEQUENCE: 3
ggaucgaaag auuccgcag gcccgaaagg guauuggcgu aggu                45

<210> SEQ ID NO 4
<211> LENGTH: 46
<212> TYPE: RNA
<213> ORGANISM: Artificial
<220> FEATURE:
<223> OTHER INFORMATION: Synthetic oligonucleotide: dFx

<400> SEQUENCE: 4
ggaucgaaag auuccgcau ccccgaaagg guacauggcg uuaggu               46

<210> SEQ ID NO 5
<211> LENGTH: 45
<212> TYPE: RNA
<213> ORGANISM: Artificial
<220> FEATURE:
<223> OTHER INFORMATION: Synthetic oligonucleotide: eFx

<400> SEQUENCE: 5
ggaucgaaag auuccgcgg ccccgaaagg ggauuagcgu uaggu                45

<210> SEQ ID NO 6
<211> LENGTH: 47
<212> TYPE: RNA
<213> ORGANISM: Artificial
<220> FEATURE:
<223> OTHER INFORMATION: Synthetic oligonucleotide: aFx

<400> SEQUENCE: 6
ggaucgaaag auuccgcac ccccgaaagg gguaaguggc guuaggu              47

<210> SEQ ID NO 7
<211> LENGTH: 77
<212> TYPE: RNA
<213> ORGANISM: Escherichia coli
<220> FEATURE:
<221> NAME/KEY: misc_feature
<223> OTHER INFORMATION: tRNAfMet
<220> FEATURE:
<221> NAME/KEY: modified_base
<222> LOCATION: (8)..(8)
<223> OTHER INFORMATION: n is s4u (4-thiouridine)
<220> FEATURE:
<221> NAME/KEY: modified_base
<222> LOCATION: (21)..(21)
<223> OTHER INFORMATION: n is d (dihydrouridine)
<220> FEATURE:
<221> NAME/KEY: modified_base
<222> LOCATION: (33)..(33)
<223> OTHER INFORMATION: n is cm (2-O-methylcytidine)
<220> FEATURE:
<221> NAME/KEY: modified_base
<222> LOCATION: (55)..(55)
<223> OTHER INFORMATION: n is t (ribothymidine)
<220> FEATURE:
<221> NAME/KEY: modified_base
<222> LOCATION: (56)..(56)
<223> OTHER INFORMATION: n is p (pseudouridine)

<400> SEQUENCE: 7
```

```
cgcggggngg agcagccugg nagcucgucg ggnucauaac ccgaagaucg ucggnncaaa      60
uccggccccc gcaacca                                                    77

<210> SEQ ID NO 8
<211> LENGTH: 76
<212> TYPE: RNA
<213> ORGANISM: Escherichia coli
<220> FEATURE:
<221> NAME/KEY: misc_feature
<223> OTHER INFORMATION: tRNAAsn
<220> FEATURE:
<221> NAME/KEY: modified_base
<222> LOCATION: (8)..(8)
<223> OTHER INFORMATION: n is s4u (4-thiouridine)
<220> FEATURE:
<221> NAME/KEY: modified_base
<222> LOCATION: (16)..(16)
<223> OTHER INFORMATION: n is d (dihydrouridine)
<220> FEATURE:
<221> NAME/KEY: modified_base
<222> LOCATION: (20)..(20)
<223> OTHER INFORMATION: n is d (dihydrouridine)
<220> FEATURE:
<221> NAME/KEY: modified_base
<222> LOCATION: (34)..(34)
<223> OTHER INFORMATION: n is q (queuosine)
<220> FEATURE:
<221> NAME/KEY: modified_base
<222> LOCATION: (37)..(37)
<223> OTHER INFORMATION: n is t6a (6-threonylcarbamoyladenine)
<220> FEATURE:
<221> NAME/KEY: modified_base
<222> LOCATION: (39)..(39)
<223> OTHER INFORMATION: n is p (pseudouridine)
<220> FEATURE:
<221> NAME/KEY: modified_base
<222> LOCATION: (46)..(46)
<223> OTHER INFORMATION: n is m7g (7-methylguanosine)
<220> FEATURE:
<221> NAME/KEY: modified_base
<222> LOCATION: (54)..(54)
<223> OTHER INFORMATION: n is t (ribothymidine)
<220> FEATURE:
<221> NAME/KEY: modified_base
<222> LOCATION: (55)..(55)
<223> OTHER INFORMATION: n is p (pseudouridine)

<400> SEQUENCE: 8
uccucugnag uucagncggn agaacggcgg acunuunanc cguaunucac uggnncgagu      60
ccagucagag gagcca                                                     76
```